United States Patent
Swidler

(10) Patent No.: US 12,042,295 B2
(45) Date of Patent: Jul. 23, 2024

(54) SYSTEMS, APPARATUSES, AND METHODS FOR DIAGNOSIS AND TREATMENT OF TEMPOROMANDIBULAR DISORDERS (TMD)

(71) Applicant: Steven A. Swidler, Tucson, AZ (US)

(72) Inventor: Steven A. Swidler, Tucson, AZ (US)

( * ) Notice: Subject to any disclaimer, the term of this patent is extended or adjusted under 35 U.S.C. 154(b) by 0 days.

(21) Appl. No.: 18/137,204

(22) Filed: Apr. 20, 2023

(65) Prior Publication Data

US 2023/0248304 A1   Aug. 10, 2023

Related U.S. Application Data

(62) Division of application No. 17/466,814, filed on Sep. 3, 2021.

(Continued)

(51) Int. Cl.
*A61B 5/00* (2006.01)
*A61F 5/058* (2006.01)

(52) U.S. Cl.
CPC .......... *A61B 5/4542* (2013.01); *A61B 5/0053* (2013.01); *A61B 5/4571* (2013.01); *A61F 5/05891* (2013.01)

(58) Field of Classification Search
CPC ... A61B 5/4542; A61B 5/0053; A61B 5/4571; A61F 5/05891
See application file for complete search history.

(56) References Cited

U.S. PATENT DOCUMENTS 5,915,385 A * 6/1999 Hakimi .................. A61F 5/566
  128/859
6,505,625 B1 * 1/2003 Uenishi .................. A61C 7/08
  128/859

(Continued)

FOREIGN PATENT DOCUMENTS

RU   2306105   9/2007   ............. A61B 10/00
RU   2370225   10/2009  ............. A61B 17/24

(Continued)

OTHER PUBLICATIONS

Alive, "Is Your Jaw Keeping Your Body Out of Alignment—A New Therapeutic Yoga Paradigm", Dec. 22, 2016, Maria Alive Therapeutics, 4 pgs.

(Continued)

*Primary Examiner* — Nicholas D Lucchesi
*Assistant Examiner* — Hao D Mai
(74) *Attorney, Agent, or Firm* — HAYES SOLOWAY P.C.

(57) ABSTRACT

A method for diagnosis of temporomandibular disorders (TMD) and related systems and apparatuses are disclosed. In the method, a visual evaluation of the patient in a standing position is first conducted. Condyle position in ear canals of the patient is palpated during jaw movement. A hip level of the patient is evaluated when back teeth of the patient are closed. If hips are unlevel, a first spacer is inserted between front teeth of the patient. The condyle position felt in the ear canals of the patient are re-palpated during jaw movements with the first spacer in place. The patient then raises and lowers his or her body by going up on their toes, and dropping to their heels. A reevaluation of the hip level of the patient is conducted and a positive or negative TMD diagnosis is indicated based on the reevaluation of the hip level of the patient.

13 Claims, 11 Drawing Sheets

Related U.S. Application Data

(60) Provisional application No. 63/074,249, filed on Sep. 3, 2020.

(56) References Cited

U.S. PATENT DOCUMENTS

| | | | | |
|---|---|---|---|---|
| 6,530,375 | B1 * | 3/2003 | Cieslik, Jr. | A61F 5/566 |
| | | | | 128/859 |
| 6,886,566 | B2 * | 5/2005 | Eubank | A61C 7/08 |
| | | | | 128/859 |
| 6,983,752 | B2 * | 1/2006 | Garabadian | A61F 5/566 |
| | | | | 128/848 |
| 7,335,173 | B2 | 2/2008 | Swidler | A61H 23/02 |
| 7,338,459 | B2 | 3/2008 | Swidler | A61H 23/02 |
| 7,708,706 | B2 | 5/2010 | Swidler | A61H 1/00 |
| 7,918,228 | B2 * | 4/2011 | Smernoff | A61H 1/02 |
| | | | | 128/857 |
| 8,001,972 | B2 * | 8/2011 | Eubank | A61C 7/08 |
| | | | | 128/859 |
| 9,526,590 | B2 * | 12/2016 | Lucas | A61C 7/08 |
| 9,655,692 | B2 * | 5/2017 | Lucas | A61C 7/36 |
| D800,910 | S * | 10/2017 | Layzell | D24/181 |
| 10,080,680 | B2 * | 9/2018 | Magness | A61F 5/566 |
| 10,335,250 | B2 * | 7/2019 | Wen | A61C 7/08 |
| 10,357,342 | B2 * | 7/2019 | Falkel | A61C 9/0046 |
| D870,894 | S * | 12/2019 | Ross | D24/180 |
| 10,772,766 | B2 | 9/2020 | Sullivan | A61F 11/12 |
| 11,096,828 | B2 | 8/2021 | George et al. | A61H 23/02 |
| 11,364,098 | B2 * | 6/2022 | Falkel | A61F 5/05891 |
| 2011/0201970 | A1 | 8/2011 | Boyd, Sr. | A61B 5/107 |
| 2012/0028221 | A1 * | 2/2012 | Williams | A61C 5/007 |
| | | | | 433/215 |
| 2015/0238283 | A1 * | 8/2015 | Tanugula | G06F 30/00 |
| | | | | 700/98 |
| 2017/0367793 | A1 * | 12/2017 | Veis | A61C 7/36 |
| 2018/0000564 | A1 * | 1/2018 | Cam | A61F 5/566 |
| 2019/0125494 | A1 * | 5/2019 | Li | A61C 7/36 |
| 2020/0138546 | A1 * | 5/2020 | Mohrlock | A61C 7/08 |
| 2020/0323677 | A1 * | 10/2020 | Droter | A61F 5/566 |
| 2023/0065574 | A1 * | 3/2023 | Gergen, II | A61F 5/566 |

FOREIGN PATENT DOCUMENTS

| | | | | |
|---|---|---|---|---|
| RU | | 2601701 | 11/2016 | A61B 17/24 |
| WO | WO2018212681 | | 11/2018 | A61B 5/103 |

OTHER PUBLICATIONS

Blum C, "Sot and the treatment of TMJ: Why dentists and chiropractors need to work together", Journal of the California Chiropractic Association 32(3): 12-13, 2007, 3 pgs.

Blum C, "SOTO-USA's dental chiropractic position statement", The Journal of Craniomandibular Practice 22(1):1-3. Jan. 2004, 6 pgs.

Blum C, "An Overview of the Development of Chiropractic Cranial Therapy—Terminology Matters", Vertebral Subluxation Research, May 30, 2011, 6 pgs.

Bond EC, et al., "Temporomandibular Disorders: Priorities for Research and Care", The National Academies Press (DC), p. 409., 2020, 11 pgs.

Costen J, "A syndrome of ear and sinus symptoms dependent upon disturbed function of the temporomandibular joint", Ann Otol Rhinol and Laryngol 43:1-15, Mar. 1, 1934, 3 pgs.

Cuccia A & Caradonna C, "The relationship between the stomatognathic system and body posture", Clinics 64:61-66, 2008, 6 pgs.

Dworkin, et al. "Diagnostic studies of temporomandibular disorders: challenges from an epidemiologic perspective", Anesthesia progress 37(2-3):147-154, 1990, 8 pgs.

Ebrahim, et al. "The effectiveness of splint therapy in patients with temporomandibular disorders: a systematic review and meta-analysis", J Am Dent Assoc 143(8):847-857, Aug. 2012, 11 pgs.

Ferguson, et al. "Cranial osteopathy and craniosacral therapy: current opinions", Journal of Bodywork and Movement Therapies 2(1):28-37, 1997, 11 pgs.

Gelb, "Airway centric TMJ philosophy," Journal of the California Dental Association 42(8):551-562; discussion 560-552, Aug. 2014, 12 pgs.

Gesch, et al. "Association of malocclusion and functional occlusion with signs of temporomandibular disorders in adults: results of the population-based study of health in Pomerania", The Angle Orthodontist 74(4):512-520, 2004, 9 pgs.

Gesch, et al. "Association of malocclusion and functional occlusion with subjective symptoms of TMD in adults: Results of the Study of Health in Pomerania (SHIP)", The Angle Orthodontist 75(2): 183-190, 2005, 8 pgs.

Glastier, Temperomandibular dysfunction and systemic distress:, International Dentistry—African Edition 2(1):76-80, 2012, 4 pgs.

Greene, et al., "Treating temporomandibular disorders with permanent mandibular repositioning: is it medically necessary?" Oral surgery, oral medicine, oral pathology and oral radiology 119(5):489-498, May 2105, 10 pgs.

Hruby, "Management of Temporomandibular Disorders: New Opportunities for Osteopathic Medicine?", The Journal of the American Osteopathic Association 119(6):340-341, Jun. 2019, 2 pgs.

James, et al. "The significance of cranial factors in diagnosis and treatment with the advanced lightwire functional appliance", International Journal of Orthodontics—Milwaukee—14(3):17-17, 2003, 7 pgs.

Kahn, et al. "The jaw epidemic: recognition, origins, cures, and prevention", BioScience, vol. 70, No. 9, Sep. 2020, 13 pgs.

Levy, "Clinical implications of mandibular repositioning and the concept of an alterable centric relation in dentistry", Basal facts 4(4):103-122, 1975, 22 pgs.

McKeown et al., "Cranio-facial changes and mouth breathing", Irish Dentist, Jun. 2011, 3 pgs.

Mew, "Science versus empiricism", British Dental Journal 199(8):495-497, Oct. 2005, 3 pgs.

MWD&W, "Bite off? Jaw off? Hips off?", Mar. 20, 2018, Medicine Wheel Dental & Wellness Center, 3 pgs.

MWD&W, "How to effectively Treat TMJ", Mar. 20, 2018, Medicine Wheel Dental & Wellness Center, 3 pgs.

Niswander, "Further studies on the Xavante Indians VII. The oral status of the Xavantes of Simoes Lopes", American Journal of Human Genetics 19(4):543-553, Jul. 1967, 11 pgs.

Ohrbach, et al. "Biopsychosocial Aspects of Orofacial Pain", Contemporary Oral Medicine, ed al FCe), pp. 1-21, 2017, 21 pgs.

Ohrbach, et al. "Premorbid and concurrent predictors of TMD onset and persistence", Eur J Pain 24(1);145-158, 2020, 25 pgs.

Peck, "Biomechanics of occlusion—implications for oral rehabilitation", Journal of oral rehabilitation 43(3):205-214, Mar. 2016, Abstract Only.

Schiffman, et al. "Diagnostic criteria for temporomandibular disorders (DC/TMD) for clinical and research applications: recommendations of the International RDC/TMD Consortium Network and Orofacial Pain Special Interest Group", Journal of Oral & Facial Pain and Headache 28(1):6, 2015, 40 pgs.

Shimshak, et al. "Health care utilization by patients with temporomandibular joint disorders", Cranio 16(3):185-193, 1998, Abstract Only.

Silveira, et al. "The increased prevalence of malocclusion in modern humans: An integrative review", EC Dental Science 17(12):2097-2107, 2018, 11 pgs.

Slade, et al, "Painful temporomandibular disorder; Decade of discovery from OPPERA studies", J Dental Res 95:1084-1092, 2016, 9 pgs.

Still, "The Philosophy and Mechanical Principles of Osteopathy", Hudson-Kimberly Pub. Co., Kansas City, MO, 1902, 318 pgs.

Türp, et al. "Dental occlusion: a critical reflection on past, present and future concepts", Journal of Oral Rehabilitation 35(6):446-453, 2008, 9 pgs.

Upledger, "TMJ: Primary problem, or tip of the iceberg?", Massage Today.com., 2021, 4 pgs.

(56) References Cited

OTHER PUBLICATIONS

Wiens JP, "A progressive approach for the use of occlusal devices in the management of temporomandibular disorders", *General Dentistry* 64(6):29-36, December 2016, Abstract Only.
Invitation to pay Additional Fees issued in PCT/US21/49113 dated Nov. 2, 2021, 2 pgs.
International Search Report and Written Opinion issued in PCT/US21/49113 dated Dec. 16, 2021, 10 pgs.
U.S. Appl. No. 17/466,814 filed Sep. 3, 2021, Swidler.
Ayouni, et al., "Comorbidity between fibromyalgia and temporomandibular disorders: a systematic review", *Oral Medicine, OOOO*, vol. 28, No. 1, Jul. 2019, 10 pgs.
Baldini A, et al. "Gnathological postural treatment in a professional basketball player: a case report and an overview of the role of dental occlusion on performance", Annali di Stomatologia, 2012, 2:51-58, 8 pgs.
Begg, et al., "Stone Age Man's Dentition: with reference to anatomically correct occlusion, the etiology of malocclusion, and a technique for its treatment", *Am. Journal of Orthodontics*, 1954, 15 pgs.
Blum, "Biodynamics of he Cranium: A Survey", *The Journal of Craniomandibular Practice*, vol. 3, No. 2, Mar.-May 1985, pp. 1640-171, 8 pgs.
Blum, "SOTO-USA's Dental Chiropractice Position Statement, Chiropractice and Dentistry in the 21st Century: Guest Editorial", *The Journal of Craniomandibular Practice*, 22(1): 1-3, Jan. 2004, 8 pgs.
Bracco, et al., "Effects of different jaw relations on postural stability in human subjects", *Neuroscience Letters* 356, 2004, 3 pgs.
Calixtre et al., "Manual therapy for the management of pain and limited range of motion in subjects with signs and symptoms of temporomandibular disorder: a systematic review of randomised controlled trials", *Journal of Oral Rehabilitation*, vol. 32, 2015, 15 pg.
Clark, et al."Sixty-eight years of experimental occlusal interference studies: What have we learned?", *The Journal of Prosthetic Dentistry*, vol. 92 No. 6, 1999, pp. 704-713, 10 pgs.
Corday, "The Relationship between Occlusion and TMD", *Open Journal of Stomatology*, 7:35-80, 2017, 46 pgs.
Colonna et al., "Comparative analysis of jaw morphology and temporomandibular disorders: A three-dimension imaging study", *Cranio*, vol. 38, No. 3, 2020, 10 pgs.
Comeaux, "Robert Fulford, DO and the Philosopher Physician", Eastland Press, 2002, 1 page abstract.
Comeaux, "Dynamic fascial release and the role of mechanical/vibrational assist devices in manual therapies", *Journal of Bodywork & Movement Therapies*, vol. 15, 2011, 7 pgs.
Corruccini, "An epidemiologic transition in dental occlusion in world populations", *Am. J. Orthol.*, Nov. 1994, 8 pgs.
Costen, "Outline of the Mandibular Joint Syndrome", 1959, 7 pgs.
Cramon-Taubadel, "Global human mandibular variation reflects differences in agricultural and hunter-gatherer subsistence strategies", *PNAS*, vol. 108, No. 49, Dec. 2011, 6 pgs.
Cuccia et al., "Manual Therapy of the Mandibular Accessory Ligaments for the Management of Temporomandibular Joint Disorders", *The Journal of the American Osteopathic Association*, vol. 111, No. 2, Feb. 2011, 11 pgs.
Dal Borgo et al., "Does asymmetry in the stomatognathic system correlate with body posture impairments? A systematic review", *South European Journal of Orthodontics and Dentofacial Research*, 2016, 3(2), 8 pgs.
Dao et al., "Oral Splints: The Crutches For Temporomandibular Disorders and Bruxism?", *Crit Rev Oral Biol Med*, 9(3), 1998, 17 pgs.
D'Ermes et al., "Influence of occlusal splint on competitive athletes performances", Annali di Stomatologia, III (3/4), 2012, 6 pgs.
Engel, "The Need for a New Medical Model: A Challenge for Biomedicine", *Psychodynamic Psychiatry*, 40(3), 2012, 21 pgs.

Friction et al., "Systematic Review and Meta-analysis of Randomized Controlled Trials Evaluating Intraoral Orthopedic Appliances for Temporomandibular Disorders", *Journal of Orofacial Pain*, vol. 24, No. 3, 2010, 18 pgs.
Gelb, et al., "The Relationship Between Jaw Posture and Muscular Strength in Sports Dentistry: A Reappraisal", *The Journal of Craniomandibular Practice*, vol. 14, No. 4, Oct. 1996, 7 pgs.
Gelb, "Clinical management of head, neck and TMJ pain and dysfunction", W.B. Saunders Co. publishers, 1985, front cover only.
Genis et al., "Comorbid Psychiatric Disorders and Treatment Options in Temporomandibular Disorders and Bruxism", *Current Approaches in Psychiatry*, 12(2), 2020, 27 pgs.
Gesslbauer, et al., "Effectiveness of osteopathic manipulative treatment versus osteopathy in the cranial field in temporomandibular disorders—a pilot study", *Disability and Rehabilitation*, vol. 40, No. 6, 2018, 6 pgs.
Gillespie, "Dental Considerations of the Craniosacral Mechanism", *Journal of Craniomandibular & Sleep Practice*, vol. 3, 1985, abstract only 2 pgs.
Girouard et al., "Treatment of Temporomandibular Joint Disorders with an Oral Orthotic Provides Postural Stabilization: A Retrospective Cohort Analysis", *Advanced Dental Technologies & Techniques*, 2020, 12 pgs.
Goose, "Changes in Human Face Breadth Since the Mediaeval Period in Britain", *Archives of Oral Biology*, vol. 26, 1981, 2 pgs.
Greene, ""The Ball on the Hill": A new perspective on TMJ functional anatomy", *Orthod. Craniofac. Res.*, vol. 21, No. 4, 2018, 5 pgs.
Greene et al., "The use of oral appliances in the management of temporomandibular disorders", *Oral Maxillofacial Surg. Clin. Of North America*, vol. 30, 2018, 13 pgs.
Grippaudo et al., "Association between oral habits, mouth breathing and malocclusion", Acta Otorhinolaryngologica Italica, 36(5), 2016, 9 pgs.
Hang, "Airway-kening Orthodontic/Orthopedic Development: A Correlation of Facial Balance, TMD, and Airway for All Ages", Springer International Publishing AG, 2018, 27 pgs.
Julia-Sanchez et al., "Dental occlusion and body balance: A question of environmental constraints?", *J Oral Rehabil.*, vol. 46, 2019, 10 pgs.
Katz et al., "Changes in human skull morphology across the agricultural transition are consistent with softer diets in preindustrial farming groups", *PNAS*, vol. 114, No. 34, Aug. 2017, 6 pgs.
Laskin et al., "Report of the President's Conference on the Examination, Diagnosis, and Management of Temporomandibular Disorders", *J. Am. Dent. Assoc.*, vol. 106, Jan. 1983, 3 pgs.
Levin et al., "Biotensegrity—The Mechanics of Fascia", Dec. 2012, 11 pgs.
Le Berre et al., "Do Adolescents With Idiopathic Scoliosis Have an Erroneous Perception of the Gravitational Vertical?", *Spine Deformity*, vol. 7, Issue 1, Jan. 2019, 6 pgs.
Macfarlane, et al., "Twenty-year cohort study of health gain from orthodontic treatment: Temporomandibular disorders", *American Journal of Orthodontics and Dentofacial Orthopedics*, Jun. 2009, 8 pgs.
Manfredini, "Current Concepts on Temporomandibular Disorders", Quintessence Publishing, Berlin, 2010, 16 pgs.
Manfredini, et al., "Dental occlusion, body posture and temporomandibular disorders: where we are now and where we are heading for", *Journal of Oral Rehabilitation*, vol. 39, pp. 463-471, 9 pgs.
Manfredini et al., "Temporomandibular disorders and dental occlusion. A systematic review of association studies: end of an era?", *Journal of Oral Rehabilitation*, vol. 33, 2017, 16 pgs.
Martins et al., "Efficacy of musculoskeletal manual approach in the treatment of temporomandibular joint disorder: A systematic review with meta-analysis", *Manual Therapy*, 2015, 9 pgs.
Maurer et al., "Strength improvements through occlusal splints? The effects of different lower jaw positions on maximal isometric force production and performance in different jumping types", *PLOS One*, 2018, 17 pgs.
Maurer et al., "Influence of the Lower Jaw Position on the Running Pattern", PLOS One, Aug. 2015, 16 pgs.

(56) References Cited

OTHER PUBLICATIONS

Mohan et al., "Occlusion: The gateway to success", *Journal of Interdisciplinary Dentistry*, vol. 2, Issue 2, May-Aug. 2012, 10 pgs.
Mohl et al., "A Textbook of Occlusion", Quintessence Publishing Co., 1988, front page only.
Moon, et al., "The Relationship Between Dental Occlusion/ Temporomandibular Joint Status and General Body Health: Part 1. Dental Occlusion and TMJ Status Exert an Influence on General Body Health", *The Journal of Alternative and Complementary Medicine*, vol. 17, No. 11, 2011, 6 pgs.
Moon, et al., "The Relationship Between Dental Occlusion/ Temporomandibular Joint Status and General Body Health: Part 2. Fascial Connection of TMJ with Other Parts of the Body", *The Journal of Alternative and Complementary Medicine*, vol. 17, No. 12, 2011, 7 pgs.
Nokar et al., "Evaluation of signs, symptoms, and occlusal factors among patients with temporomandibular disorders according to Helkimo index", *CRANIO, The Journal of Craniomandibular & Sleep Practice*, 2018, 6 pgs.
Ohlendorf et al., "The effects of a temporarily manipulated dental occlusion on the position of the spine: a comparison during standing and walking", *The Spine Journal*, vol. 14, 2014, 8 pgs.
Otsuka et al., "Influence of the TMJ position on limbic system activation—an fMRI study", Zeitschrift für Kraniomandibuläre Funktion 3(1), 2011, 13 pgs.
Palla et al., "Answer to a still open question: Temporomandibular disorders and posture", SIDO Consensus Conference, 2015, 9 pgs.
Patti et al., "The influence of the stomatognathic system on explosive strength: a pilot study", *The Journal of Physical Therapy Science*, 28: 72-75, 2016, 4 pgs.
Perinetti, et al., "Postuorgraphy as a diagnostic aid in dentistry: a systematic review", *Journal of Oral Rehabilitation*, vol. 36, 2009, 15 pgs.
Pope, "The Common Compensatory Pattern: Its Original and Relationship to the Postural Model", *The AAO Journal*, Winter 2003, 22 pgs.
Price, "Nutrition and Physical Degeneration", 8$^{th}$ Edition, Price-Pottenger Nutrition Foundation, 2009, front page only.
Priebe et al., "Stability of physical therapy effects on temporomandibular disorder", Rev Dor. São Paulo, 2015, 4 pgs.
Ramirez-Yanez, et al., "The effect of dental occlusal disturbances on the curvature of the vertebral spine in rats", *The Journal of Craniomandibular & Sleep Practice*, vol. 33, No. 3, 2015, 11 pgs.
Rinchuse et al., "Scoping review of systematic review abstracts about temporomandibular disorders: Comparison of search years 2004 and 2017", *Am. Journal of Ortho. And Dentofacial Orthopedics*, vol. 154, No. 1, Jul. 2018, 21 pgs.
Scarr et al., "Examining the temporo-mandibular joint from a biotensegrity perspective: A change in thinking", *Journal of Applied Biomedicine* 15, 2017, 8 pgs.
Scarr et al., "Resolving the problems and controversies surrounding temporo-mandibular mechanics", *Journal of Applied Biomedicine* 14, 2016, 9 pgs.
Schulze et al., "Prediction of Ergogenic Mouthguard Effects in Volleyball: A Pilot Trial", Sports Medicine International Open 2019, 6 pgs.

Scrivani et al., "Temporomandibular Disorders", *The New England Journal of Medicine*, (359) 2008, 14 pgs.
Sharma et al., "Incident injury is strongly associated with subsequent incident temporomandibular disorder: Results from the OPPERA study", *Pain*, 160(7), 2019, 23 pgs.
Sicher, "Temporomandibular articulation in mandibular overclosure", *The Journal of the Am. Dental. Assoc.*, vol. 36, No. 2, Feb. 1948, 9 pgs.
Simmons, "Why are dentists not trained to screen and diagnose temporomandibular disorders in dental school?", *CRANIO, The Journal of Craniomandibular & Sleep Practice*, vol. 34, No. 2, 2016, 3 pgs.
Sims et al., "Temporomandibular Joint Dysfunction, Trigeminal Nerve Inflammation, and Biomedical Dental Treatments for the Suppression of Neurological and Neuropsychiatric Symptoms", Springer International Publishing AG, 2018, 29 pgs.
Sims et al., "Tourette's syndrome: A Pilot Study for the Discontinuance of a Movement Disorder", *The Journal of Craniomandibular Practice*, vol. 27, No. 1, Jan. 2009, 8 pgs.
Skog et al., "Tinnitus as a comorbidity to temporomandibular disorders—A systematic review", *J Oral Rehabil.* vol. 46, ps. 87-99, 13 pgs.
Smith et al., "Problems and Methods in Research on the Genetics of Dental Occlusion", *Genetic Research*, vol. 47, No. 1, 1977, 13 pgs.
Stack, et al., "The Relationship Between Posture and Equilibrium and the Auriculotemporal Nerve In Patients with Disturbed Gait and Balance", *Journal of Craniomandibular Practice*, vol. 27, No. 4, 2009, 13 pgs.
Sutherland, "The Cranial Bowl", Free Press Company, 1939, front cover only.
Svechtarov, et al, "Primary Temporomandibular Disorders and Comorbid Conditions", Scripta Scientifica Medicinae Dentalis, vol. 2, No. 2, 2016, 5 pgs.
Swanson, "Biotensegrity: A Unifying Theory of Biological Architecture With Applications to Osteopathic Practice, Education, and Research—A Review and Analysis", *Journal of the American Osteopathic Association*, vol. 113, No. 1, Jan. 2013, 19 pgs.
"TMJ Disorders", US Department of Health and Human Services, NIH, 2017, 20 pgs.
Toro-Ibacache, et al., "Dental malocclusions are not just about small and weak bones: assessing the morphology of the mandible with cross-section analysis and geometric morphometrics", *Clinical Oral Investigations*, 2019, 12 pgs.
Türp et al., "The dental occlusion as a suspected cause for TMDs epidemiological and etiological considerations", *Journal of Oral Rehabilitation*, 39, 2012, 12 pgs.
Turvey et al., "The Medium of Haptic Perception: A Tensegrity Hypothesis", *Journal of Motor Behavior*, vol. 46, No. 3, 2014, 46 pgs.
Upledger, et al., "Craniosacral Therapy", Eastland Press, 1983, 1 page abstract.
Yunus, "Fibromyalgia and Overlapping Disorders: The Unifying Concept of Central Sensitivity Syndromes", *Semin Arthritis Rheum* 36(6), 2007, 18 pgs.

* cited by examiner

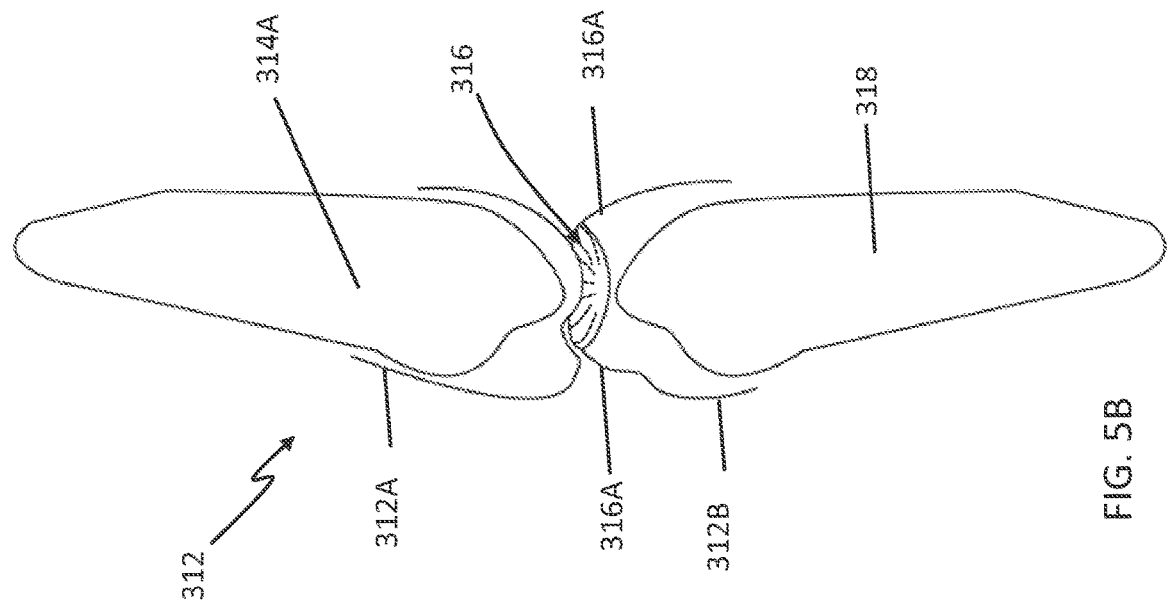
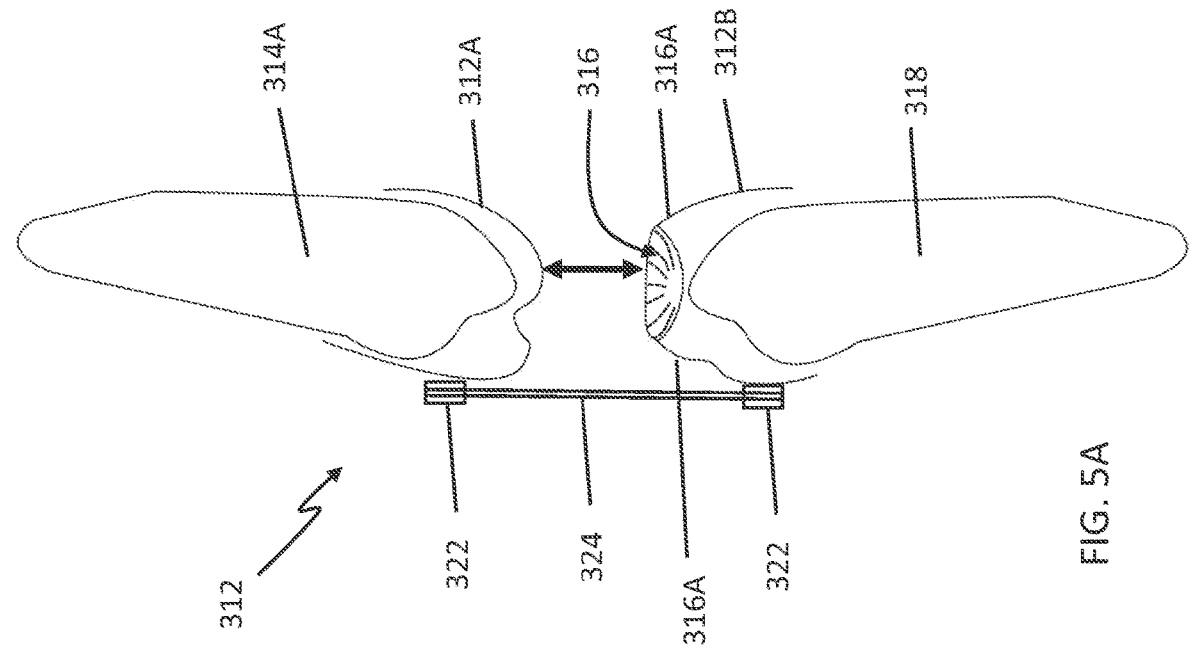

SYSTEMS, APPARATUSES, AND METHODS FOR DIAGNOSIS AND TREATMENT OF TEMPOROMANDIBULAR DISORDERS (TMD)

CROSS REFERENCE TO RELATED APPLICATION

This application is a divisional of U.S. patent application Ser. No. 17/466,814 entitled "Systems, Apparatuses, and Methods for Diagnosis and Treatment of Temporomandibular Disorders (TMD)" filed Sep. 3, 2021, which claims benefit of U.S. Provisional Patent Application Ser. No. 63/074,249 entitled, "Systems, Apparatuses, and Methods for Diagnosis and Treatment of Temporomandibular Disorders (TMD)" filed Sep. 3, 2020, the entire disclosure of which is incorporated herein by reference.

FIELD OF THE DISCLOSURE

The present disclosure is generally related to the diagnosis of medical conditions and more particularly is related to systems, apparatuses, and methods for diagnosis and treatment of temporomandibular disorders.

BACKGROUND OF THE DISCLOSURE

Temporomandibular disorder (TMD) is a complex set of conditions related to the jaw joints or temporomandibular joints (TMJs). Classic TMD with localized symptoms is considered a major cause of pain and dysfunction worldwide, second only to back pain (and related to it), with an annual cost in the USA of $4 billion. Dentists are uniquely tasked with diagnosis, since they can differentiate tooth pain from TMD musculoskeletal pain, but TMD treatment is usually not emphasized in the dental curriculum, nor is there a medical specialty available for professional referral of TMD patients, with the result of high dissatisfaction by the public of the mixed results they receive even from dental TMJ specialists. The most common symptoms of TMD include localized pain in the TMJ and masticatory muscles (spontaneous or upon palpation), limited jaw movements, and noise (popping, crepitations or clicking) in the TMJ, but there are additionally a vast number of correlated comorbid body conditions associated with TMD, including: fibromyalgia, irritable bowel syndrome, chronic fatigue syndrome, body and joint pain, excessive daytime sleepiness, and psychosocial disorders. Top conditions reported for TMD often include anxiety, depression, headaches, neckaches, insomnia, fatigue and body pain.

Although TMD has been considered benign and self-limiting, some researchers paint a more bleak picture: the individuals in chronic pain have been described as existing in a "liminal" state of neither being truly "ill" in the eyes of society nor truly "healthy", and those in pain begin to lose their "sense of self". The research into TMD spans across multiple disciplines—dentistry, psychology, neurology, chiropractic, osteopathy, manual medicine, complementary and alternative medicine, fascia research, otology, optometry, and even veterinary and animal studies. However, despite the extensive research into TMD, there are conflicting reports with how pervasive it is. Some believe that TMD affects 5-7% of the population whereas others, depending on the methodology used, report ranges between 6-93%.

Early studies of TMD suggested that malocclusion, including overclosure, and lack of vertical dimension from missing teeth and other factors were related to the cause of TMD, and treatment consisted of resetting the patient's dental occlusion and replacing missing teeth. However, several large-scale studies reported little causal (and variable correlational) evidence for misaligned teeth/malocclusion, and/or orthodontic treatment and TMD symptoms, and the prevailing opinion is that TMD has little to do (clinically) with occlusion or with posture, but not always. The current prevailing school of thought is that TMD has a multifactorial etiology and is predominately biopsychosocial. A recent well-designed prospective study built on the assumption of a biopsychosocial model, has identified multiple risk factors (present before TMD diagnosis), most importantly self-reports of "jaw parafunction" and presence of comorbid conditions. The upshot is that TMD appears to be causatively associated with the cumulative effect of multiple system dysregulation. But, after nearly 100 years of study, there remains no generally agreed upon etiology for TMD, no generally-agreed upon test or treatment for differential diagnosis, or even an agreement as to why the jaw joints are so unusually associated with overall pain and distress.

The TMJs are often described as the most complicated joints in the body. The paired joints are tucked behind the bony arches of the cheekbones on either side of the face, just forward of the ear canal. They connect the mandible to the temporal bones, are innervated by the large trigeminal nerve, and are located in a high priority neurological region— a swath of the head between the forehead and chin accounting for about 40% of motor/sensory nerves in the cortex of the brain. They are unusual among the synovial joints in having both a hinge and sliding movement and is the only joint to have a "hard copy" end point established by how the teeth come together (occlude). Furthermore, the unique feature of TMJ is that this joint is one of the only bilateral joints that crosses the midline— other than the cranial bones, SI joints and spinal vertebrae. One can move any one-sided joint such as an arm, leg, hip, and so on without moving the opposite corresponding joint. This is highly significant if the temporal bones are not coordinated moving in their very subtle balanced equal and opposing motion. Also, one cannot move the right TMJ without moving the left TMJ which has many implications in fascial connections, neuroanatomy, and neurophysiology.

The TMJs are part of the stomatognathic system, consisting of the teeth, jaws and associated tissues. The mandible is suspended in a sling fashion by fascia, ligaments and muscles to the hyoid bone, collarbone, and skull. In normal function and motion, it accommodates the big functional movements of the jaw: chewing, swallowing, social communication including speaking, posturing, facial expression, and is controlled by multiple different muscle groups. The teeth touch approximately 2,000 times a day when chewing and swallowing, and these contacts can increase significantly with parafunctional habits (clenching, grinding, etc.) exacerbated by physical and emotional stress. Curiously, and unlike the other synovial joints, there is a high variability in the placement of the moving part of the joint (condyle) due to variations in the bite growth, and development that sets that position. For example, over a lifetime, the joint survives the eruption of baby teeth, permanent teeth, growth of the mandible into the late teen years, variations of occlusion due to wear, orthodontics, tooth loss, and later age related bone loss, as well as person-to-person variations in tooth-based occlusion (CO or MI maximally intercuspated position, malocclusion classes I, II and III) and other joint positioned classifications (CR and 4/7 joint positioning). There is much controversy over the structural details that are considered normal in the recommended conservative treatment of occlusion.

Dental orthotics are commonly used in the treatment of TMD, and they remain the most applied treatment, but there is little agreement about design, or even if orthotics are needed given the impression by some investigators of a generally benign nature of the disease. Orthotics are thought to help to deprogram the effects of the teeth touching each other in a posterior jaw position by avoiding the triggering of occlusal interferences in a bite that is off, helping retain jaw positive awareness, and by alleviating the tremendous forces from parafunctional habits such as clenching and grinding (which deliver much more loading to the jaw joint itself).

Historically and biomechanically, the jaw has been modeled as a lever. A limitation of these traditional models is that, although the Newtonian mechanics is correct, they limit study to the jaw joint itself and do not take into account the individual motion of all of the cranial bones, whole body alignment, and other yet undiscovered subtle mechanisms of feedback and compensations. A truer model is tensegrity where the jaw is a significant component of the whole-body system of bones, muscles, and fascia/connective tissue. Here the bones are seen as "struts" pivoting against each other in a fascial and muscular environment of tension and compression. The tensegrity model of biomechanics opens the door for new approaches and ideas: for example, there is a resurgence of osteopathic and chiropractic approaches in conjunction with tensegrity. Another idea is one of tensegrity combined with haptics— like the almost intuitive connection with using a cell phone, or a spider within its web, haptic perception may be operating within the very subtle palpation and treatment skills of cranial osteopathy.

The idea of compensatory mechanisms can also be reframed as a mechanism of tensegrity, which are affected or modified by each person's zone of adaptability or tolerance in each moment. The jaw joint in relation to a therapeutic approach that includes the system of fascia has been explored and recognized as a significant structural component. Long explored but little developed, is the effect of the cranial bone movement in relation to the temporomandibular joint and dentistry as a primary foundational influence. The jaw and jaw joint position, if displaced posteriorly or if asymmetrical can alter or impinge on motor and sensory signaling to the entire body and its interconnecting with the fascial and musculoskeletal tensegrity system and vice versa. And, in an even bigger picture, we know that movement facilitates the human (and animal) need to survive, to orient in space and gravity, find mates, and food and avoid danger. If the jaw joints are displaced posteriorly it is like the tuner of a radio being half a station off and creating neurological "static" throughout the body systems. Indeed, as the TMJ is deeply embedded in the area of the head representing the area in the body with the highest concentrated zone of nerves and nerve distribution, it is not surprising the temporomandibular joints are involved in multiple interconnected systems affecting the whole body.

Thus, a heretofore unaddressed need exists in multiple fields and industries to address the aforementioned dysfunctions, deficiencies, and developmental inadequacies.

SUMMARY OF THE DISCLOSURE

Embodiments of the present disclosure provide a system, apparatuses, and methods for diagnosis of temporomandibular disorders (TMD). Briefly described, in architecture, one embodiment of such a method, among others, can be broadly summarized by the following steps: providing a patient; conducting a visual evaluation of the patient; palpating condyles in ear canals of the patient during jaw movement; evaluating a hip level of the patient when back teeth of the patient are closed completely; inserting a first spacer between front teeth of the patient; re-palpate condyles in the ear of the patient during jaw movements with the first spacer in place; raising and lowering the patient by movement of the patient standing on toes and dropping to heels; reevaluation of the hip level of the patient; and indicating a positive or negative TMD diagnosis based on the reevaluation of the hip level of the patient.

The present disclosure can also be viewed as providing a dental orthotic apparatus for aiding recovery from TMD. Briefly described, in architecture, one embodiment of the apparatus, among others, can be implemented as follows. A first shell is sized to substantially fit over an upper set of teeth of a patient. A second shell is sized to substantially fit over a lower set of teeth of a patient, the first and second shells being removable from the upper and lower sets of teeth of the patient, respectively, wherein the first and second shells are frictionally held on the upper and lower sets of teeth of the patient, respectively. At least two cuspid indents are formed in the second shell in a location substantially corresponding to a position of upper cuspid teeth of the patient when a jaw of the patient is closed, wherein protruding ends of the upper cuspid teeth of the patient are positioned at least partially within the at least two cuspid indents during jaw closure to align a jaw joint position of the patient by stabilizing mandibular condyles of the patient into a centralized relationship.

The present disclosure can also be viewed as providing a durable dental orthotic system for aiding recovery from TMD. Briefly described, in architecture, one embodiment of the system, among others, can be implemented as follows. A first durable shell is sized to substantially fit over an upper set of teeth of a patient. A second durable shell is sized to substantially fit over a lower set of teeth of a patient, the first and second shells being removable from the upper and lower sets of teeth of the patient, respectively, wherein the first and second shells are frictionally held on the upper and lower sets of teeth of the patient, respectively. At least two cuspid indents are formed in the second shell in a location substantially corresponding to a position of upper cuspid teeth of the patient when a jaw of the patient is closed, wherein protruding ends of the upper cuspid teeth of the patient are positioned at least partially within the at least two cuspid indents during jaw closure to align a jaw joint position of the patient by stabilizing mandibular condyles of the patient into a centralized relationship. A durable material is inlayed or overlayed to at least one of the first and second durable shells in a location corresponding to a contact point between the first and second durable shells, wherein the durable material is a different material type than the first and second durable shells.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 5A-5B are diagrammatical illustrations of a dental orthotic to improve TMD, in accordance with the second exemplary embodiment of the present disclosure.

DETAILED DESCRIPTION

To improve over the conventional methods of diagnosing and treating TMD, this disclosure is directed to a multidisciplinary integrative team approach to diagnosing and treating TMD using techniques from the dental, cranial osteopathic, and bodywork fields. In particular, the combined use of palpation— a highly sensitive haptic skill set—in cranial osteopathy, manual medicine and dentistry have been found to be an effective tool at diagnosing and treating TMD. This new approach, to achieve what may be referred to as the 'Centralized Ideal (CI) Occlusion' is a functional jaw joint position that affects the entire body and is based on the osteopathic principle of structure as the mechanical cause of disease. As discussed in greater detail herein, to achieve CI Occlusion, it is possible to use dental orthotics that are adjusted by palpation testing—referred to as the 'Pinky Test'—to evaluate the patient's hips as the "most sensitive indicator" for a TMD differential diagnosis. This method/technique may provide postural stability of the TMJs, cranial base, and hips while the patient undergoes a treatment program of fascia/whole body release work, cranial osteopathic manipulation, and movement retraining therapy.

Figure 1:
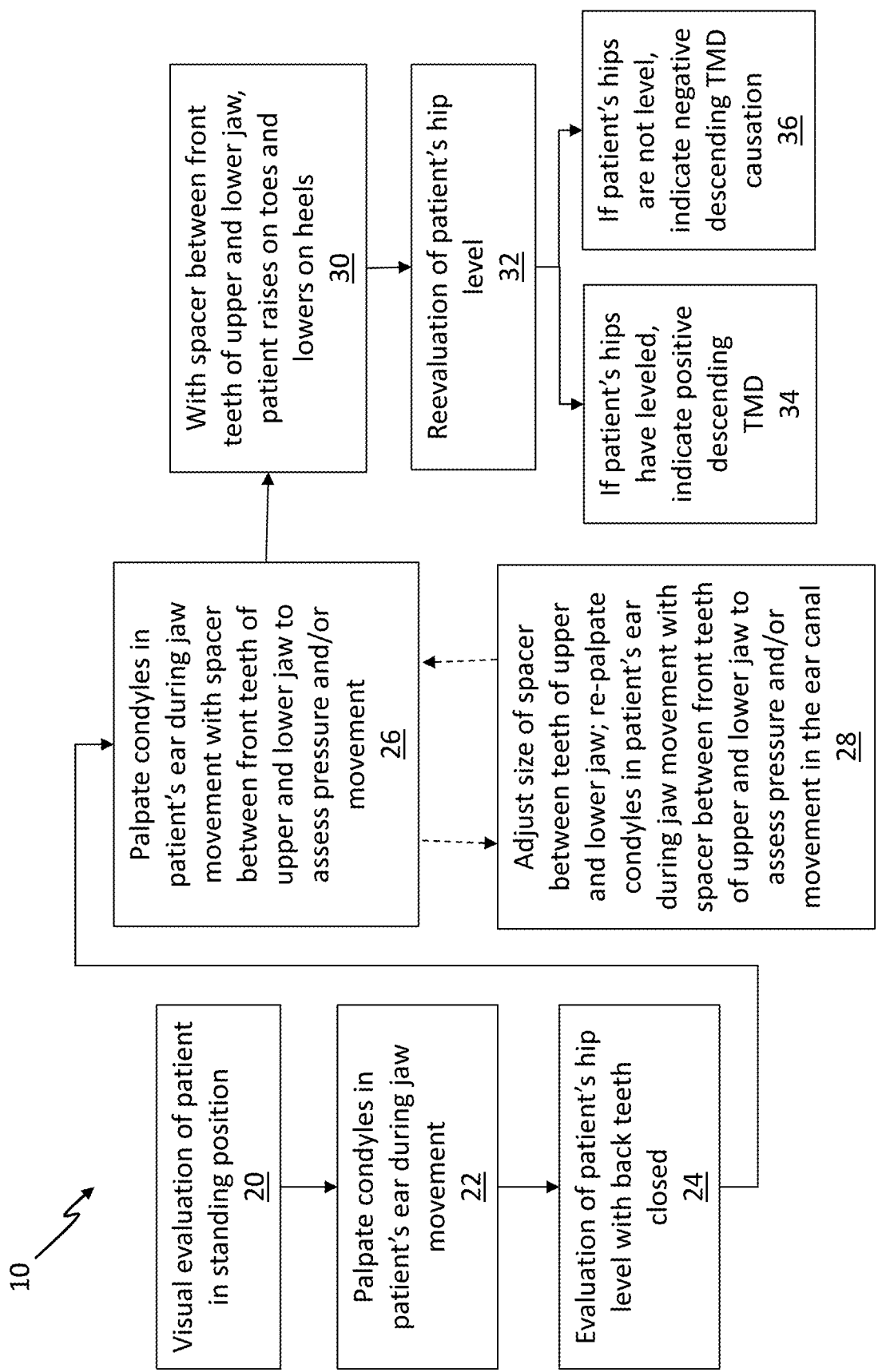
FIG. 1 is a flowchart illustrating a method for diagnosis of TMD, in accordance with the first exemplary embodiment of the disclosure.

FIG. 1 is a flowchart 10 illustrating a method for diagnosis of TMD, in accordance with the first exemplary embodiment of the disclosure. In particular, this method describes the Pinky Test which uses palpation along with the newly discovered concept of a jaw-hip interrelationship to show how TMD can be diagnosed based on the level of the patient's hips, e.g., whether the patient's hip on one side of their body is horizontally level with the other. Manual medicine, such as chiropractic, osteopathic, osteopathic manipulative medicine (OMM), and others, recognizes level hips as the foundation for an erect body alignment of the spine. Accordingly, there is a great focus to identify the causative factors for un-level hips. There are two general causes of hip level destabilization: ascending and descending contributing factors. Ascending contributing factors disrupt hip alignment from the hips or below. These may be due to old injuries of the leg, twisted ankles, knee injuries, pubic shear, or similar conditions. Descending contributing factors come from above the hips. Clinically, a patient often has both factors, but one is typically predominant or primary. In this sense, a positive Pinky Test is detecting a descending causative issue (+/−90%), while an absence of hip leveling and jaw position correction suggests a potential ascending (5%) causative issue.

The Pinky Test differs from most dental procedures, which are performed with the patient sitting in the dental chair and do not take into account the entire body's self-aligning and compensatory mechanisms. In contrast, this test is performed with the patient standing, and uses the practitioner's small or "pinky" fingers to palpate for any movement of the condyles in the ear canals, while the patient opens wide and closes in their habitual bite, and following after biting on a spacer, such as a cotton swab or stick, anteriorly placed between their upper and lower front teeth edge to edge bringing the jaw forward and more open. If un-level hips level with repositioning, the test is positive for a descending TMJ involvement. In the majority of patients, one hemi pelvis is rotated forward and the other is rotated backward, but the hips need to be aligned and level to the horizon for optimum balance, posture, function, and nerve signaling. It has been found that level hips are more highly associated with centralization of the jaw joint when movement of the jaw joint is not palpable in the ear canal. Thus, there are three possible outcomes of the Pinky Test: a positive result indicated by a high hip that levels with jaw repositioning; a negative result indicated by a high hip that does not level with jaw repositioning; or no result which is indicated by already existing level hips. The methodology described herein can serve not only as a diagnostic tool, but also for guiding treatment for centralizing the jaw joint, establishing CI occlusion, and guiding the integrative team approach to TMD described herein.

Referring to FIG. 1, it should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 20, the process may begin with a preliminary evaluation of the patient assuming a standing position. Here, the patient removes their shoes to avoid the influence of worn shoes with already established imbalanced wear patterns. Standing on a level floor, the patient may move their body up and down on their toes a couple of times and land on their heels to achieve a neutral postural baseline. Then, the evaluator evaluates their posture noting the level of the eyes, ears, shoulders, clavicles. After receiving permission, the evaluator may palpate the patient's hips on the iliac crests at the mid-seam of the body, e.g., along the patient's shirt seam. If the hips are uneven, the test continues to the next step.

Figure 2:
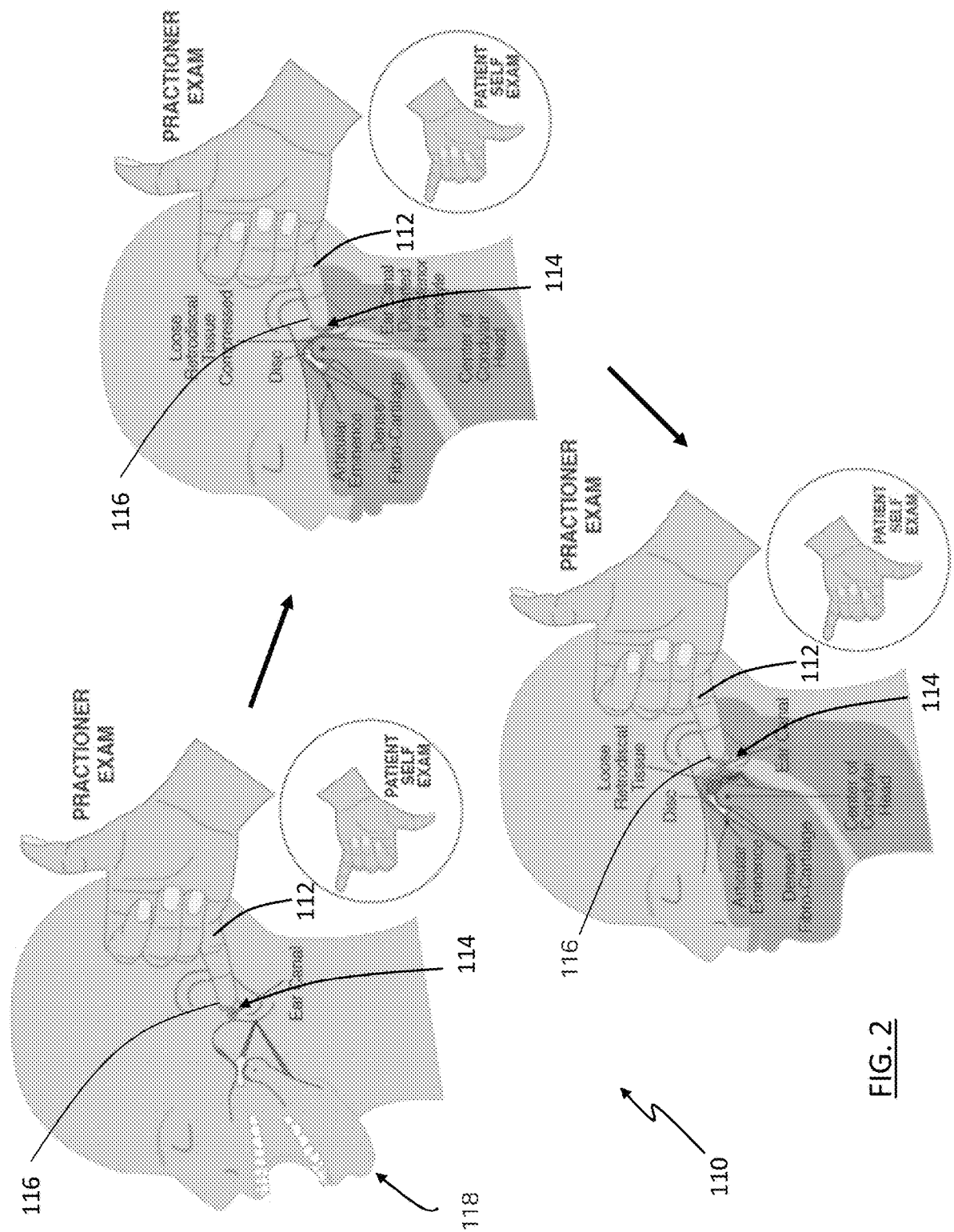
FIG. 2 is a diagrammatical illustration of the method for diagnosis of TMD, in accordance with the first exemplary embodiment of the present disclosure.

Next, in block 22, the evaluator palpates the condyles in patient's ear during jaw movement of the patient. This step is illustrated in the diagram 110 of FIG. 2. Specifically, with the evaluator facing the patient, the evaluator places each of their fingers, and ideally, their two pinky fingers 112 well, but comfortably, into the patient's ear canals 114. The evaluator's hands should be positioned with his or her thumbs facing upwards so that the pads 116 of the fingers 112 are facing the condyles of the patient (and facing the evaluator too). The patient then opens their mouth 118 wide and closes on their back teeth several times, while the evaluator notes any pressure, movement, or sounds by tactile feeling with his or her pinkies. If loose retrodiscal tissue is compressed by the condylar head, the evaluator may feel the ear canal distorted by the posterior condyle. The evaluator also observes how the patient's jaw moves and deduces whether there are any deviation or restriction in motion. It is noted that it is possible to conduct a self-exam, where the evaluator's hands are positioned inverted, such that their thumb extends downwards and the pad 116 of their pinky finger 114 is facing forward.

Next, at block 24, with the patient still standing, the evaluator sits or kneels down in front of the patient so the evaluator can achieve a position where they are substantially eye-level with the patient's hips. In this position, the evaluator can visually determine if the hips are level when the patient's back teeth remain fully closed. Then, the evaluator may place the first knuckle of his or her index finger on the hip bone with palms parallel to the floor and all fingers flat together facing straight back, on the hip bones at the shirt seam of the body. The evaluator can then determine which side of the patient's hips is higher than the other, at which point the evaluator removes his or her hands from the iliac crests of the patient. While visual and/or tactile methods of detection may be used, it is noted that other methods for determining hip level may be used, such as evaluation at ASIS or PSIS.

Figure 3:
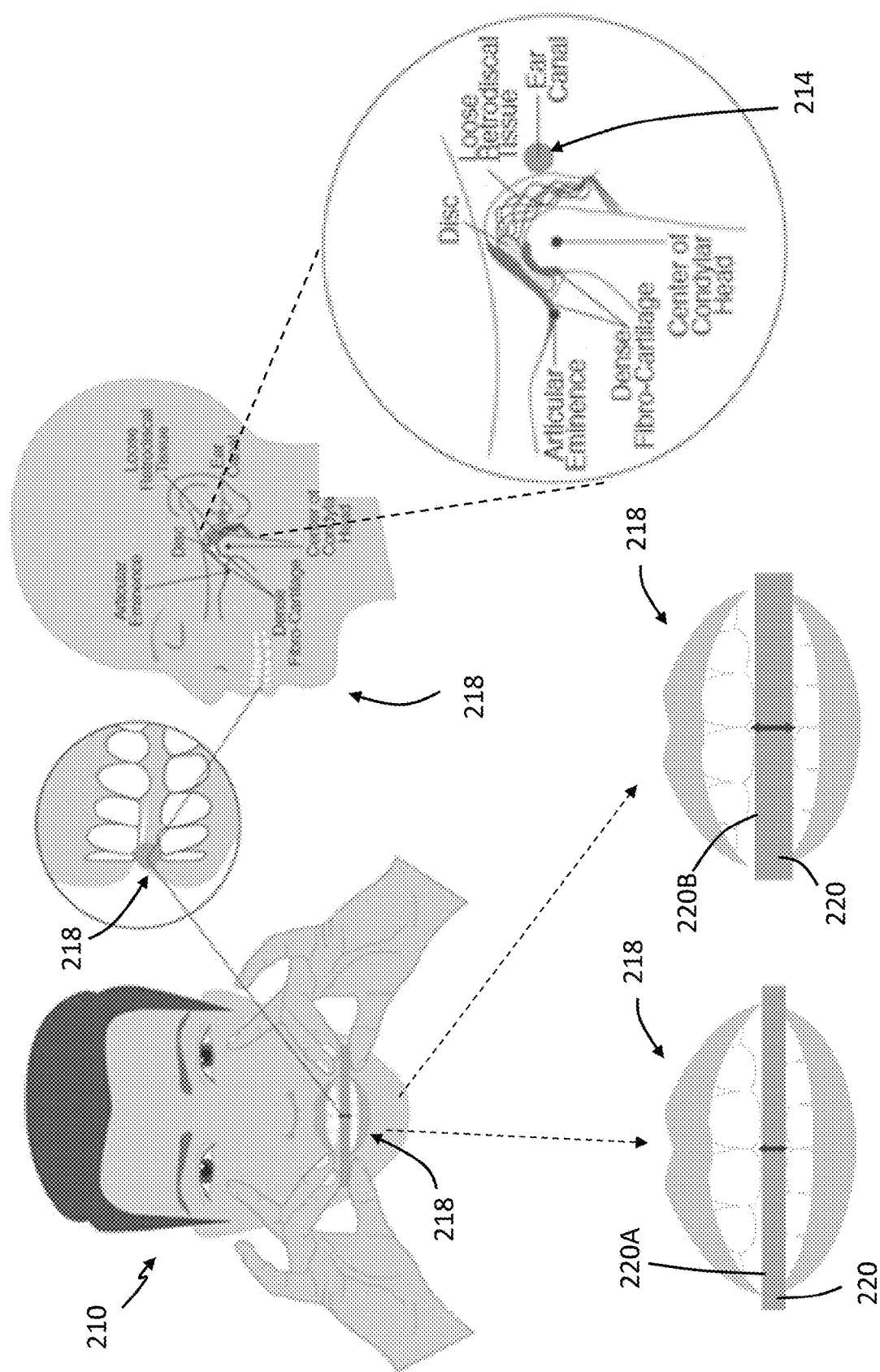
FIG. 3 is a diagrammatical illustration of the method for diagnosis of TMD, in accordance with the first exemplary embodiment of the present disclosure.

The next step, as shown at block 26, is illustrated in the diagram 210 of FIG. 3. Here, the evaluator palpates condyles in patient's ear canal 214 with the pad 116 of their finger 112 during jaw movement (FIG. 2) and while the patient has a spacer 220 between their teeth. The spacer 220 may be a thin spacer 220A or a thicker spacer 220B between front teeth of upper and lower jaw 218, which allows the evaluator to assess pressure and/or movement of the condyle on the pinkies with the jaw in a more anteriorized or open (increased vertical) position. The patient's jaw is moved forward so the upper and lower front teeth edges rest on the spacer 220. The spacer 220 may be an object which can be positioned between the patient's front upper and lower front teeth edges and bitten down upon safely, such that the upper and lower jaw are spaced further apart from each other than during a normal bite without the spacer 220. In one example, the spacer 220 may be a cotton swab or a medical stick, such as a tongue depressor. The spacer 220 is placed between the upper and lower front teeth edges, which may cause the patient's jaw to move forward. The patient may hold the spacer 220 in place by maintaining the spacer in contact on the upper front teeth edges. For stability, while the evaluator's fingers 112 will again be palpating in the ear canal 214, the patient may place the pads of their index fingers on their cheeks and hold the ends of the spacer on each side with their thumbs and third fingers of each hand for stability. While the spacer 220 remains touching the upper two front teeth, the patient opens wide, and shuts closed with front teeth on the spacer so that the evaluator can palpate the condyle motions in the ear canal 214. The evaluator determines if, with the spacer in place, the audible or palpable indicators of the jaw, such as popping and clicking, have gone away after a few openings and closings. The evaluator also determines if there is less pressure and/or movement noticed on his or her fingers 112.

As shown at block 28 of FIG. 1, this process may be repeated with differently sized spacers. Specifically, the evaluator may remove the first spacer and insert a larger or smaller spacer into the patient's jaw 218 and then re-palpate condyles in patient's ear during jaw movement with spacer positioned between front teeth of upper and lower jaws. The evaluator continues to assess pressure, sounds and/or movement of the patient's condyles. The evaluator may repeat the process any number of times using differently sized spacers until he or she detects that the pressure and/or movement of the patient's condyles on the practitioner's pinkies have changed, improved, or otherwise been altered, along with audible evaluation of any popping or clicking noises. Ideally no pressure or movement should be felt when the jaw joint position is centralized. Additionally, if the patient has undergone orthodontic treatment and the bone in the joint has been remodeled, pressure or movement of the joint may not be palpable even when the jaw joint position is centralized, however, the change in hip level is still consistent.

Once an ideally sized spacer is located, the patient keeps the spacer between his or her front teeth of upper and lower jaw and raises and lowers their body on their toes, as shown at block 30 in FIG. 1. In this step, the patient rests his or her upper and lower front teeth edges on the spacer with midlines lined up, but secondary to a position where opening and closing results in no palpable motion simultaneously in both ear canals. This can be evaluated by having the patient very slightly move their jaw side to side while front teeth remain resting on the spacer, while the evaluator notices how the upper and lower teeth midlines line up when there is no motion in either ear simultaneously. The evaluator then removes his or her pinkies from the patient's ears and asks the patient to again raise up and down on their toes while biting on the spacer. The evaluator then rechecks the level of the hips, as shown at block 32. If the patient's hips have achieved a horizontally level position, this is an indication that a descending TMJ misalignment is a dominant influence, which is an indication of a positive diagnosis of TMD, as shown at block 34. If the patient's hips are still not horizontally level, this is a negative indication for a primary descending cause, e.g., an indicator of a negative diagnosis of TMD, as shown at block 36. In this case, it is likely that the patient may have a potential ascending issue, or a mix of ascending/descending causative factors.

Figure 4A:
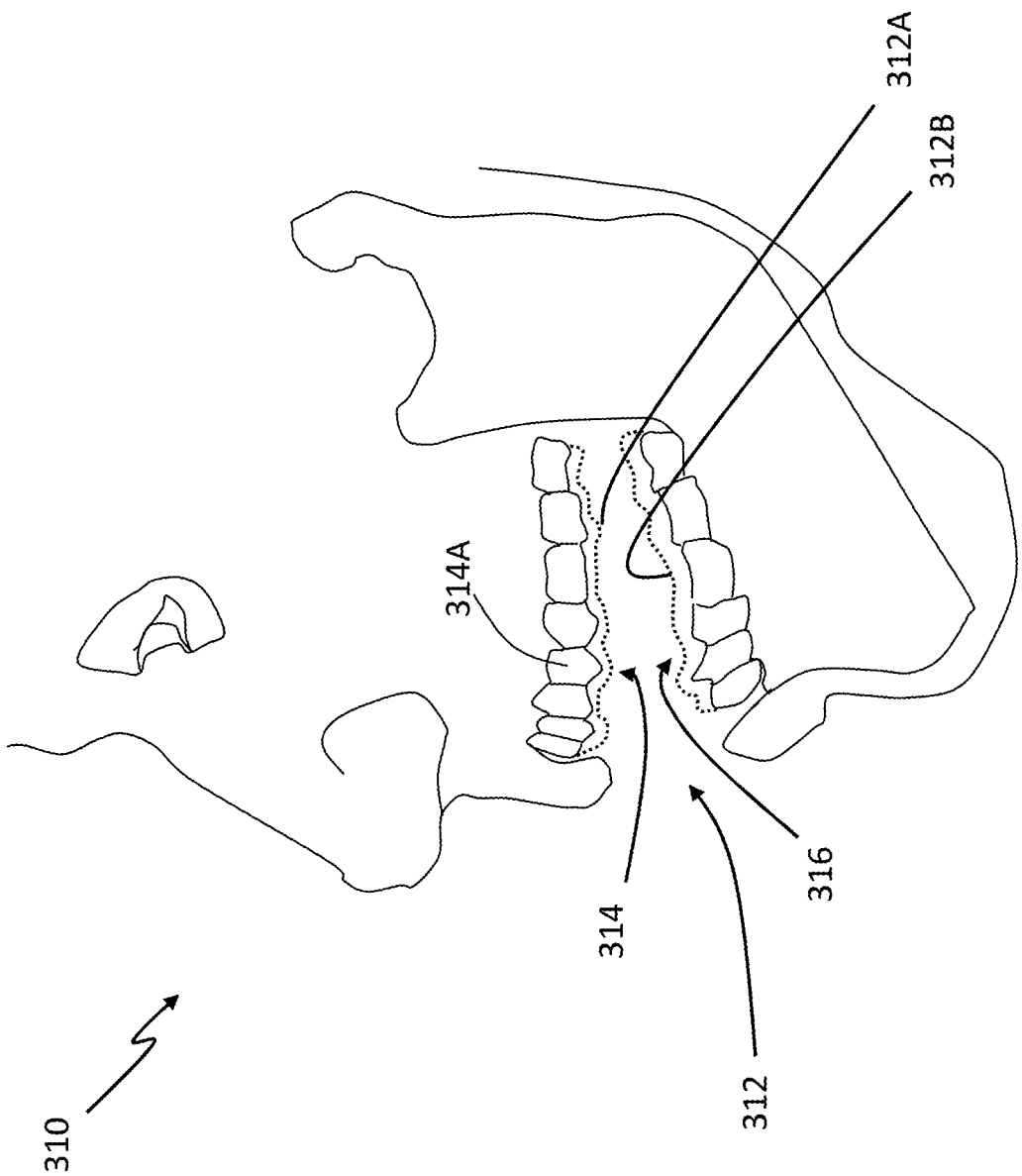
FIG. 4A is a cross-sectional illustration of a human jaw with a dental orthotic to improve TMD, in accordance with a second exemplary embodiment of the present disclosure.

The Pinky Test, as described herein, may be used to provide a diagnosis of TMD. In order to aid a patient in recovery from TMD, this disclosure also contemplates a dental orthotic apparatus and system which can be used by dentists and other medical practitioners to alleviate TMD pain and improve a patient's condition. FIG. 4A is a cross-sectional illustration 310 of a human jaw with a dental orthotic 312 to improve TMD, in accordance with a second exemplary embodiment of the present disclosure. As shown, the dental orthotic 312 (which is shown enlarged for detail) may be positioned on the patient's teeth on the lower and/or upper jaws. As shown, an upper dental orthotic shell 312A is positioned to frictionally fit over the set of teeth on the patient's 310 upper jaw while a lower dental orthotic shell 312B may be positioned to frictionally fit over the set of teeth on the patient's 310 lower jaw. The upper and lower dental orthotic shells 312A, 312B may be formed from a sufficient material, such as plastic, which is preferably transparent or clear such that the orthotic device 312 is less visibly noticeable. It may also be possible to use a more cosmetic and durable orthotic after CI Occlusion has been stabilized.

The upper dental orthotic shell 312A maintains a frictional fit over the patient's teeth, such that the patient's upper cuspid teeth 314A, or canine teeth, which normally have a protruding and extended position relative to the adjacent teeth in the upper jaw, are covered by the upper dental orthotic shell 312A with the contour of the upper dental orthotic shell 312A not obstructing the normal, protruding shape of the upper cuspid teeth 314A. On the patient's lower jaw, a lower dental orthotic shell 312B is positioned over the patient's teeth. The lower dental orthotic shell 312B has two cuspid indents 316 which are positioned in a location on the patient's lower jaw corresponding to the upper cuspid teeth 314A. The cuspid indents 316 are cavity structures which have a recessed position within the lower dental orthotic shell 312B, such that they form a bowl-shape which can receive the protruding ends of the patient's upper cuspid teeth 314A when the patient's jaw is closed. The bowl shape of the cuspid indents 316 is formed with sidewalls of the cuspid indents 316 being positioned higher than a middle interior portion of the cuspid indents 316. When the patient closes their jaw, the two cuspid indents 316 are capable of receiving the protruding ends of the upper cuspid teeth 314A, respectively, therein. When the patient bites down, the contact of the cuspid indents 316 and the protruding ends of the upper cuspid teeth 314A may act to correct the alignment of the jaw, as described further in detail here.

Figure 4B:
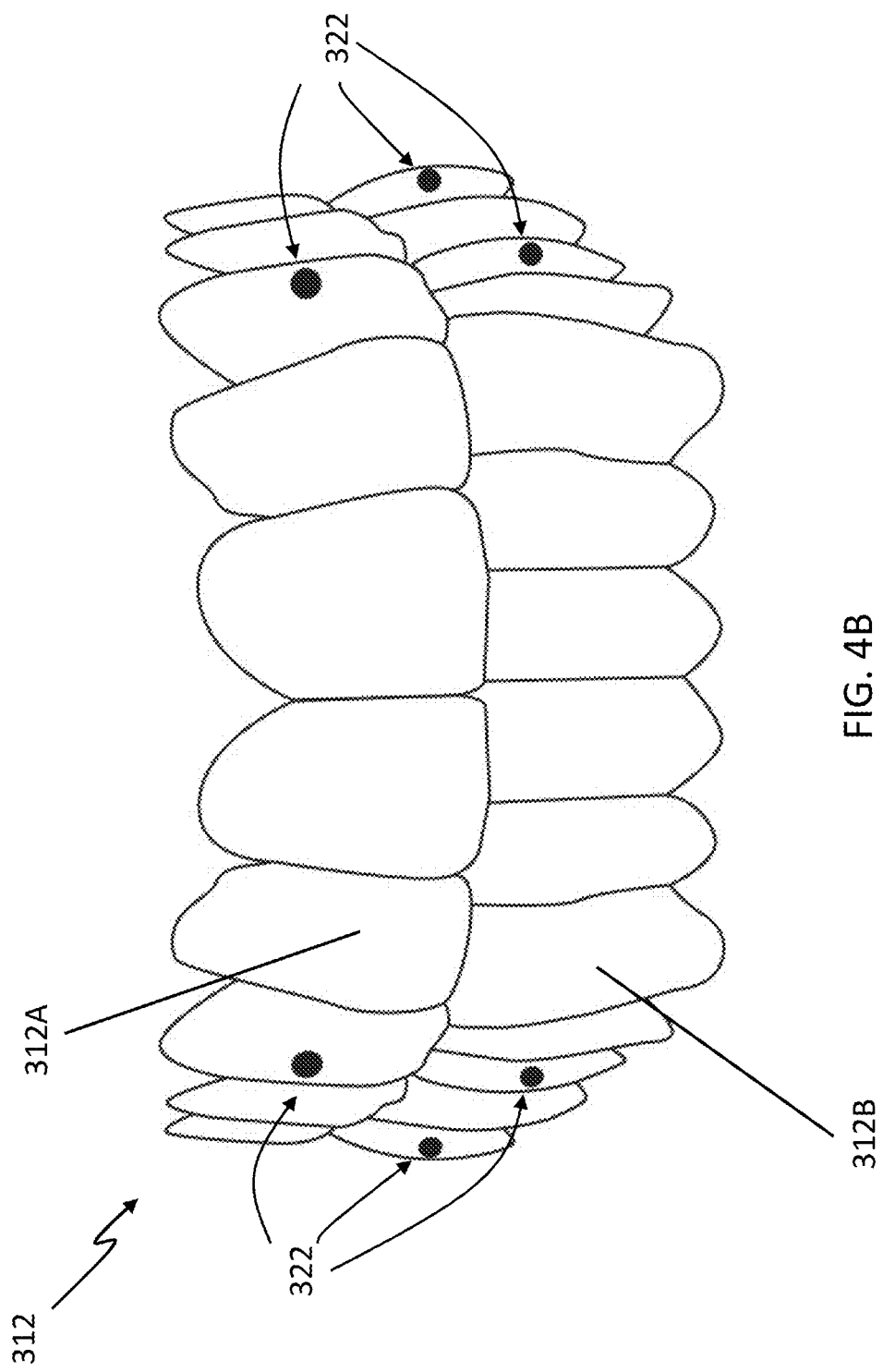
FIGS. 4B-4D are images of a dental orthotic to improve TMD, in accordance with the second exemplary embodiment of the present disclosure.
Figure 4C:
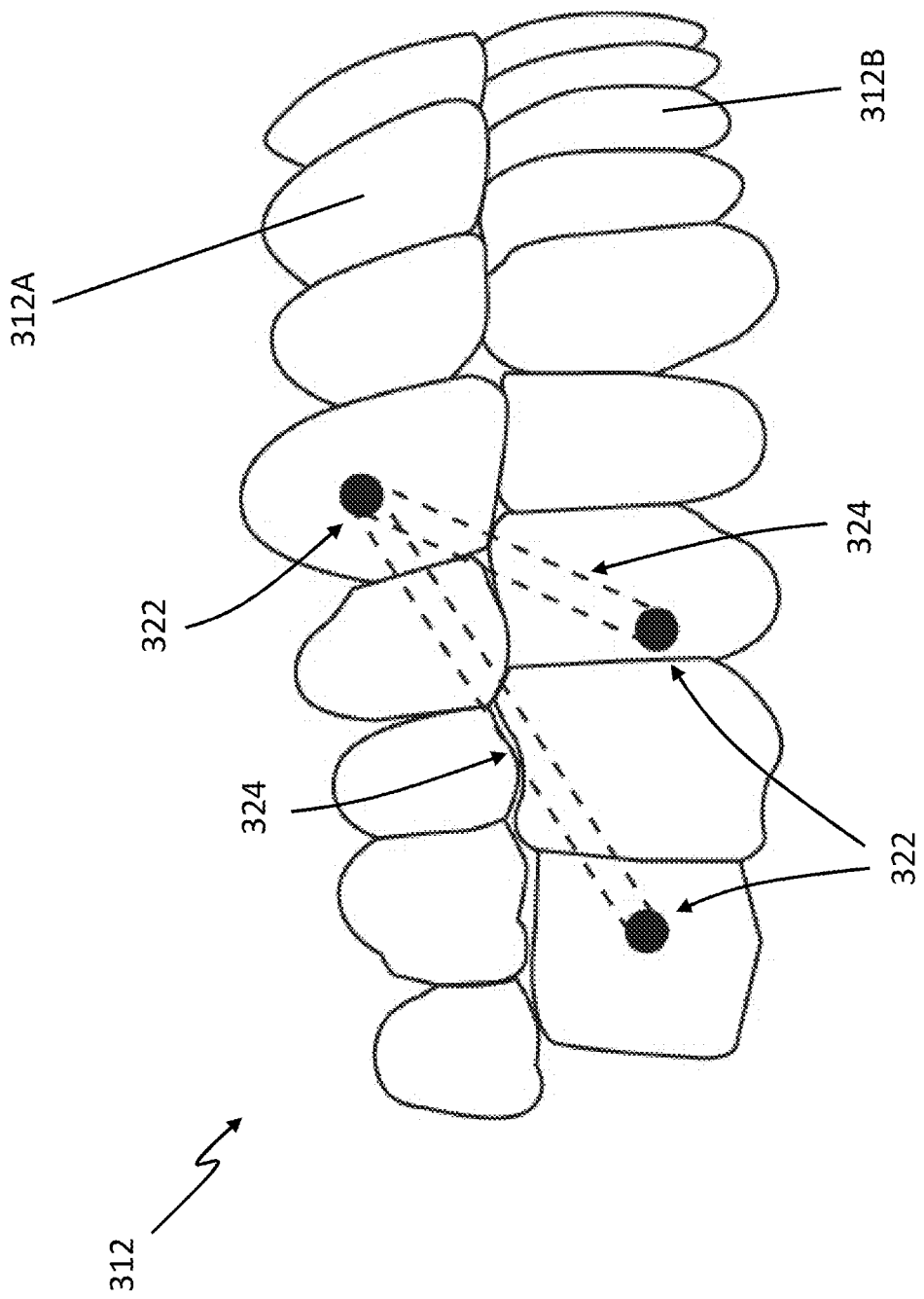
Figure 4D:
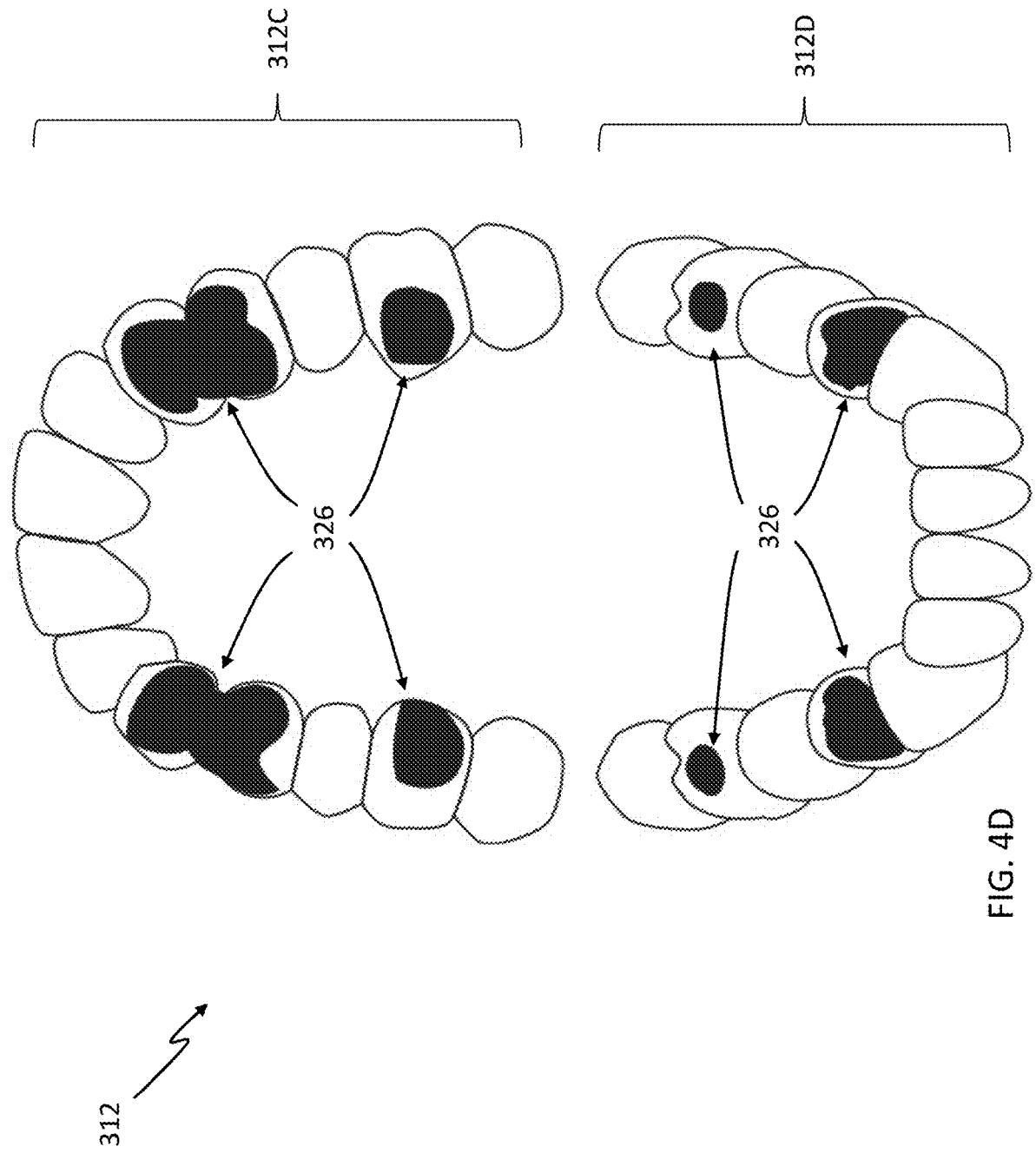

While the specific design of the dental orthotic 312 may vary, FIGS. 4B-4D are illustrations of the dental orthotic shells 312A, 312B to improve TMD, in accordance with the second exemplary embodiment of the present disclosure. As shown, the dental orthotic shells 312A, 312B provide full arch coverage of the patient on the upper and/or lower jaws. The dental orthotics shells 312A, 312B may be constructed from plastics or similar materials to ergonomically fit over the patient's teeth. The dental orthotics shells 312A, 312B may have one or more buttons 322 that may be positioned on the sides of the dental orthotics shells 312A, 312B to allow for an elastic band 324 or similar material to connect between the upper and lower dental orthotics shells 312A, 312B primarily for nighttime use. The buttons 322 and the elastic bands 324 may allow the jaw to rest forward instead of dropping back in gravity, impinging on the airway. The position of the buttons 322 and the elastic bands 324 may vary, depending on the design of the apparatus, but in one example shown in FIG. 4C, a button 322 may be positioned on the upper cuspid tooth 314A of the upper jaw and buttons 322 may be positioned on rear teeth of the lower jaw.

After the upper and lower dental orthotics shells 312A, 312B have been utilized to establish CI occlusion so that the body is in its best postural and functional alignment and the cranial bones are all moving in an unrestricted equal and opposing subtle cranial motion, it may be necessary to utilize a second, more durable appliance. For example, the clear, upper and lower dental orthotics shells 312A, 312B may initially be manufactured from lighter-weight plastics, such that they can be used by the patient during the day, if necessary, and not overly obstruct normal oral activities of the patient or look too noticeable. Once CI occlusion is established, a new set of the upper and lower dental orthotics shells 312C, 312D may be used which are more durable to ensure that proper treatment can continue. As shown in FIG. 4D, these durable upper and lower dental orthotics shells 312C, 312D may be an occlusal alignment appliance which is used to create a minor crossbite in the cuspid area with rotated lower cuspids to guide the jaw forward as the bite closes fully with the lower cuspid tip slightly in front of the upper cuspid and to then carry lateral excursions (left and right) movements of the jaw on the cuspids and bicuspids which are all functionally splinted together by the whole arch appliances.

As can be seen in FIG. 4D, the functional surfaces of the durable upper and lower dental orthotics shells 312C, 312D, as well as a posterior occlusal stop, contact in the molar area on both sides at contact points 326. As such, to prevent excessive wear or misalignment, these contact points 326 are all created with a hardened material, such as white ceramic (zirconia) inlays and onlays embedded in the removable upper and lower orthotics shells 312C, 312D which overlay the patient's teeth. The hardened material used, such as zirconia, is a different material type than the material used to construct the shells 312C, 312D, such as a plastic or similar material. The contact points 326 may be formed in a white color to match the white color of the durable upper and lower dental orthotics shells 312C, 312D which may be formed from polymer and/or resin. The backside (lingual) surfaces of the rotated cuspids on the lower and the hardened contact points 326 on the lower first bicuspids just behind them form a centering cup, much like the cuspid indents of the clear treatment appliances, so that the inside (lingual) cusps of the upper first bicuspids (also fitted with white hardened onlays) fit into this functional lower cup while the minor crossbite created by the rotated cuspids guides full closure of the teeth into a forward jaw position that centralizes the jaw joint when the bite is fully closed (maximum intercuspation).

The use of the durable upper and lower dental orthotics shells 312C, 312D was conceived after studying a wide variety of primate skulls where the lower cuspid "fangs" are in front of the upper teeth. With this set up the cuspids function against each other with the jaw in a more forward position (allowing for much thicker bone between the jaw joint and ear canal than in humans). Meanwhile back teeth are not worn flat-like a cow chewing side to side without cuspids. The cuspids are aligned to separate back teeth so that the teeth are not worn flat. The cuspids carry the side to side motion with what in dentistry is referred to as cuspid guidance. The minor rotation and slight crossbite creates a cosmetically acceptable functional alignment to accomplish jaw joint anteriorization without resorting to the large cuspid fangs of primates.

FIGS. 5A-5B are diagrammatical illustrations of a dental orthotic 312 to improve TMD, in accordance with the second exemplary embodiment of the present disclosure. In particular, these figures illustrate the interconnection between the upper cuspid tooth 314A and the cuspid indent on the lower dental orthotic 312B/312D. FIG. 5A shows the dental orthotic 312 when the patient's jaw is opened and FIG. 5B illustrates the patient's jaw in a closed position. As can be seen, in FIGS. 5A-5B, the lower dental orthotic shell 312B/312D has the cuspid indent 316 which is positioned aligned with the protruding end of the upper cuspid tooth 314A covered by the upper dental orthotic shell 312A/312C. When the jaw is in the open position, the protruding end of the upper cuspid tooth 314A is positioned substantially near the cuspid indent 316, such that when the jaw is closed, as shown in FIG. 5B, the protruding end of the upper cuspid tooth 314A can enter the cuspid indent 316. This acts to align the upper jaw with the lower jaw of the patient when the patient's jaw is in the closed or partially closed position.

As can be seen in FIGS. 5A-5B, the cuspid indent 316 may have two or more lateral sidewalls 316A, or more preferably, is shaped as a cavity or bowl with a continuous sidewall. The sidewall 316A is positioned or substantially aligned with the top lateral sides of the protruding end of the upper cuspid tooth 314A. In one example, the cuspid indents 316 may also be open along a length of the set of teeth, i.e., along the front and back of the tooth, such that the constraint of the cuspid protrusion 314 is only for lateral movement of the jaw. In another example, as depicted in FIGS. 5A-5B, the cuspid indents 316 may have sidewalls positioned on all sides of a tooth 318, so as to form a cavity for receiving the protruding end of the upper cuspid tooth 314A and constraining motion of it in lateral, forward, and rear directions. Also shown in FIG. 5A are the buttons 322 which are positioned on the dental orthotic shells 312A, 312B (or 312C and 312D) such that a rubber band 324 or similar biasing structure can attach thereto.

To construct a dental orthotic 312, it is assumed that the level hips are the most sensitive indicator for a centralized functional jaw joint position on the articular eminence. Then, based on the Pinky Test, as described relative to FIGS. 1-3, it is possible to take a measurement to assess the distance and angle between upper and lower dental arches required to level the hips. In a typical patient, the hips level when absolutely no motion or sounds of the mandibular condyles is detectable by palpation within the ear canal. In general, repositioning the jaw joint relationship can be accomplished by two methods: either by increasing the vertical (thicker spacer), or moving the chin more forward, anteriorizing the jaw. It may be preferred to use the most cosmetic combination where no motion is detected. For dentists, with the patient standing and with the jaw in the appropriate position, a bite material is syringed in between the back upper and lower teeth, and over the front teeth (including any spacer) to capture the relationship, or the bite position and upper/lower arch relationship can be registered with a digital scanner. It is now possible to mount and orient models for creating a lower orthotic to stabilize the jaw relationship in that position. The orthotic fills in the space between the upper and lower back teeth created when resting the front teeth edges on the appropriate sized spacer.

The beginning dental orthotics 312 may be designed with cuspid indents located in the lower cuspid area to receive the upper cuspid protrusions to stabilize in this position. These indents, which the outer portion can be later removed to allow for chewing, if desired/indicated, will centralize the patient's jaw joint each time she or he closes or swallows into it, like lowering a vertical pin hitting anywhere on the inside of an upright funnel. This helps the patient to know where to go with their bite and jaw position and provides a new "hard copy" end point for their bite closure and jaw joint positioning. The orthotic is designed to stabilize the mandibular condyles into a centralized jaw joint position. A lower orthotic is preferred as it does not restrict the inherent motion of the upper six bones of the maxilla. Overall, the teeth should only touch each other or the orthotic when chewing or swallowing. If indicated, a separate guard for nighttime use can be used to encourage the jaw to relax, with bilateral elastics upper to lower, positioning the jaw forward like resting the jaw in a hammock.

Figure 6A:
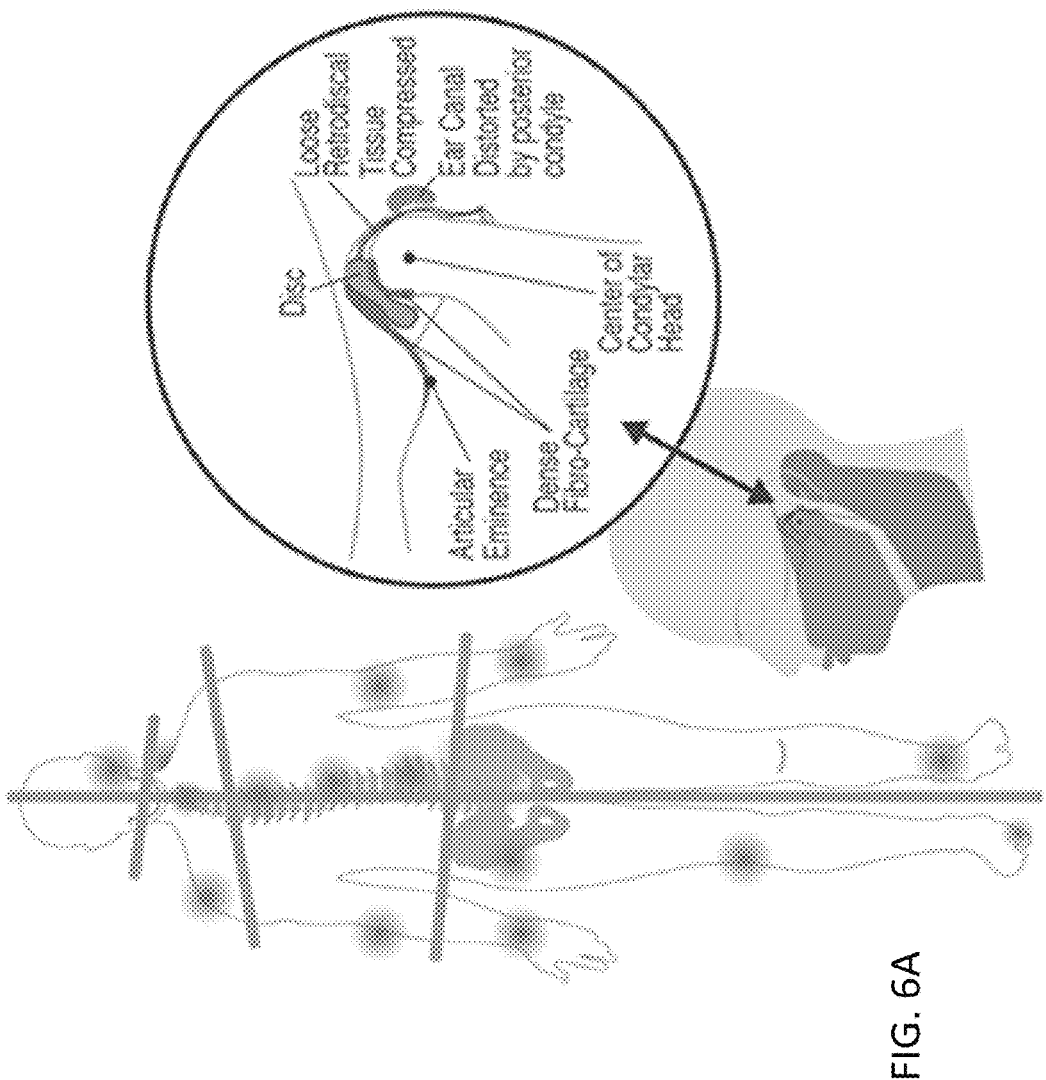
FIGS. 6A-7 are illustrations of diagrams representing the Triplet's Body Relationship in accordance with a third exemplary embodiment of the present disclosure.
Figure 6B:
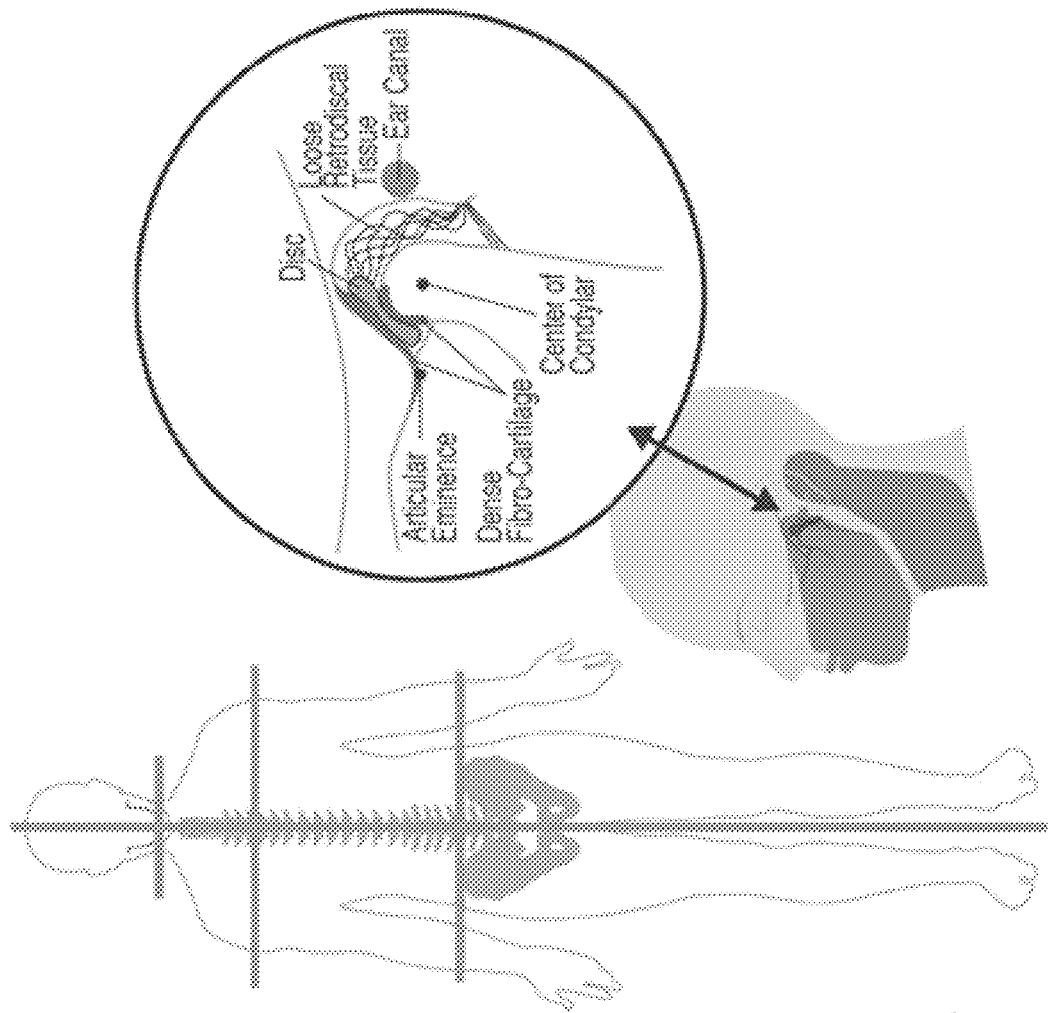
Figure 7:
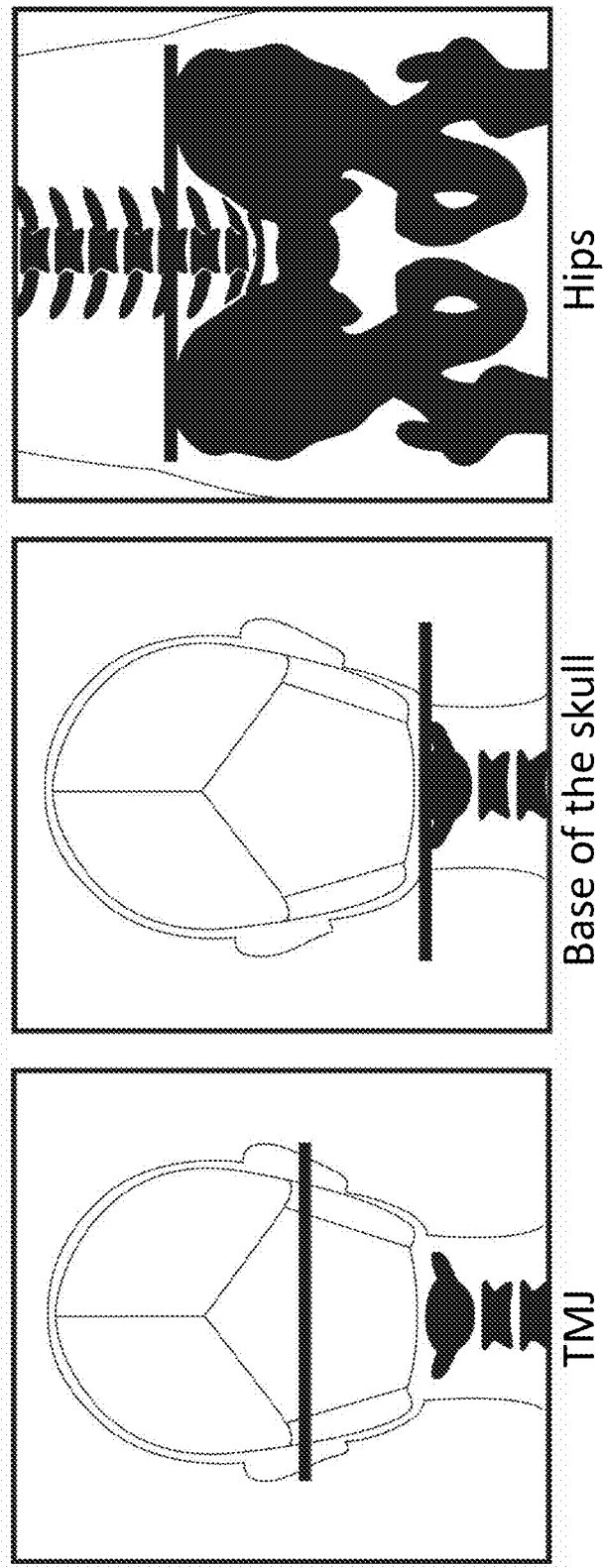

As described herein, the interrelationship between the jaw and the hips can be used to evaluate patients for TMD, and the evaluation can be used to provide a dental orthotic to aid in relief from TMD symptoms. In addition to this discovery, the inventors of this disclosure also discovered an interrelationship between the jaw, the cranial base, and the hips, which is described herein as the 'Triplet's Body Relationship.' FIGS. 6-7 are illustrations of diagrams representing the Triplet's Body Relationship in accordance with a third exemplary embodiment of the present disclosure. In particular, FIG. 6A illustrates the dysfunctional posterior jaw joint position prior to treatment, where the misaligned points of the patient's body are visible. As can be seen, the patient has a smaller, retruded chin. In contrast, FIG. 6B illustrates a healthy centralized jaw joint position after treatment where the hips have leveled and the points of the patient, namely at the jaw, the chest, and the hips, have aligned. In FIG. 6B, the patient has a fuller chin posture. FIG. 7 illustrates a detailed image of the alignment shown in FIG. 6B, in particular, depicting the alignment of the TMJ, the base of the skull, and the hips.

It is well established in Chiropractic wisdom that when one vertebra of the spine is "off" it will affect the other vertebrae at the opposite end of the spine. Specifically, the Lovett brother or twin brother relationship is this "so above, so below" phenomenon which says if C1 is off in alignment, L5 is off, and if C2 is off, L4 is off, C3 to L3, C4 to L2 and so forth. A similar Triplet's body relationship has here been identified between the cranial base and the TMJ and how it affects hip alignment, such that when the jaw is off, the cranial base is off, and the hips are off. While the exact cause of this is not confirmed, it is believed that one possible answer is found through anatomy and proximity. In the adult, the most internal aspect of the glenoid fossa (the socket of the TMJ) is approximately 1.3 inches from the occipital condyles where the base of the head rests on, and articulates with, C1 of the spine. Another consistent observation is that when the cranial base is off, the displaced atlas (C1) impinges on the Vagus nerve on one side. Impingement here affects the heart, respiration, and digestion. Because of these effects, it is crucial to routinely check the cranial base and hips (as major "circuit breakers"), and correct any structural misalignment there before adjusting the dental orthotics.

It is also important to consider cranial bone movement, as the temporal bones ("T" of the TMJs) need to be freely moving through their unrestricted subtle motions. With patients having TMD, it may be useful to measure cranial rhythm, which is typically 3-4 times per minute and can be felt very subtly throughout the body. This fluid motion matches the palpable fluctuation of the cerebrospinal fluid moving up and down the spine. For the TMJ to function optimally, the fluid motion of the temporal bones must be simultaneously unrestricted, and balanced side-to-side. The temporal bones are designed to move in an equal and opposing fashion like the "gills of a fish". A restricted temporal bone on one side of the jaw alters the shape and angle of the jaw joint itself, thus creating an imbalance with the opposite temporal bone, which distorts the angle of the TMJ function. By changing the relationship of the jaw in its socket on that side, it can also affect balance caused by mismatched sensory signals from the paired sets of semi-circular canals on each side of the head located in the paired temporal bones, as well as affect the oculo-vestibular reflex both of which provide feedback to the brain to help keep us upright and oriented vertically in gravity.

In addition to the cranial osteopathic assessments/methods described herein, it has also here been discovered that a restricted temporal bone on one side of the head directly relates to a one-sided opposite excursion of the lungs. This palpatory evaluation can be palpated with the patient supine and placing the palms under the body on either side of the patient's mid thoracic spine. In health, with inhalation both hands will be subtly carried downward, and with exhalation, both hands will move subtly towards the patient's head. With a restricted temporal bone on one side, the lungs move palpably in opposite directions. Usually, but not always, this occurs on the same side. Opposite lung excursions, alone, can cut down a person's pulmonary function by up to 50%. Using osteopathic methods, it is possible to free up the motion of the restricted temporal bone and restore the normal excursions and lung capacity as well as essential to develop the parameters of CI occlusion.

It may also be beneficial to use OMM techniques or chiropractic skills to identify and release other restrictions. A restriction (a.k.a. osteopathic lesion) is what osteopaths feel as either a lack of motion, or pull, with their trained hands. Healthy fascia has a fluid gliding movement. Restrictions are biomechanical alterations such as adhesions, scars, fibrotic tissue, and strain patterns. These restrictions can affect the alignment and function of the entire body, where areas of pain and stiffness can often result from a lifetime of layers of physical trauma (sprained ankles, broken bones, arthritic joints, etc.) as well as emotional trauma, layered like an onion. It has been found that it is usually possible to reset the key structural body "circuit breakers" that tend to go off and free up the cranial bones (as described previously) and this usually creates immediate relief of stiffness, pain and restores an enhanced range of motion. To release restrictions, hands-on techniques are employed as well as percussion tools that a patient can use for self-care. It may also be effective to use a Body Percussion Table (also invented by the inventor) which was designed to aid in unwinding and release of whole-body fascial strain patterns. It can be used for either preparing the body tissue for manual treatment in about 12 minutes (eliminating 70% of the compensation patterns and interferences) or after treatment to globalize the effect of manual treatment releases throughout all the body tissues.

As a patient progresses through treatment, and as releases are accomplished, and normal unrestricted cranial bone motion is restored, the orthotic bite is able to be kept aligned as indicated by level hips. It may also be beneficial for the patient to meet with a movement specialist to assess posture and movement, and to develop better alignment and body use patterns. Para-function is a term often applied to the mouth with issues such as nail biting, clenching and grinding. These, and habitual body misuse patterns are what a patient needs to become aware of to discontinue. The first week of an appliance worn in the daytime is very useful consciously training for this biofeedback to carry into nighttime use. The movement specialist then designs a program tailored to each patient's needs and habit patterns. Referrals depending on what is needed for that individual, may be made directly to specific members of the integrative team including: personal trainers, physical therapists, psychologists, yoga therapists, dance and rhythm therapists, etc. reinforcing balanced expanded movement, now with improved equilibrium, posture and flexibility.

It is further noted that proprioception, haptic integration, and balance in gravity may need to be accounted for during treatment. Patients may experience pain during treatment, namely an occasionally sharp, but more often dull, achy, chronic and fatiguing, and related to low energy or brain fog. Instantaneous resolution of these symptoms may occur upon adjustment of the dental orthotic to level, balancing the hips. Many of these patients also suffer from vertigo, balance issues, lack of eye focus, and may also benefit from vision therapy using adjustable corrective lenses that reflect improved body and cranial alignment. Like unevenly worn shoes, corrective vision prescriptions are usually created to a body and cranial relationship that is out of alignment. Reevaluating the corrective visual prescription is best done after or while CI is established.

While the full complement of physiological mechanisms underlying the Triplet's jaw-cranial base-hip interrelationship are unknown, as it is applied while the patient is standing, it likely involves, in part, the neurological responses for maintaining an upright posture in gravity. When the signals are mismatched from eyes, ears, and proprioceptors, the brain and neuromuscular system becomes overworked attempting to compensate and maintain an upright posture in gravity. Scoliosis has been associated with an altered sense of the vertical, which might involve "dysfunction of trunk graviceptors." If 90% of the population is lacking a functional jaw-hip response, as suggested by clinical observations, this would explain why comorbid TMD symptoms and early functional scoliosis (directly associated with unlevel hips) has not been previously discovered to be existing at such an epidemic level. Balanced jaw, cranial base, and hip relationships also support improved brain function and clarity.

As with most dysfunctions, one must also consider the possibility that other contributing factors are an influence, and these may be physical, mental, emotional, or spiritual. TMD is associated with a multitude of psychosocial symptoms including: depression, anxiety, panic attacks, self-effacing thought forms (patterns), fear, avoidance, catastrophizing, and somatization. As described above, the mental health of patients may improve as their physical symptoms improve. In addition, patients may be able to use various self-help mechanisms to relieve physical and/or psychosocial symptoms.

As previously described, there are many classifications of dental occlusion, and most are based on a static and localized view of the oral system. In the past, dental schools have taught only two classifications of occlusion: CO (centric occlusion) a tooth-based relationship identification where your teeth most fit together habitually (now called MI—for maximally intercuspated position). The second, a jaw-joint based relationship, CR (Centric Relation) occlusion can be established by forcing the jaw back and up into its most superior, posterior position. Authorities of the time had touted the value of this as being a more reproducible position by having an end point pivot stop reference. These old systems of classification no longer serve us if we are to consider the impact of neuromuscular balance and body jaw alignment relationships that are relying on observations guided by the response of spontaneous alignment of the hips. Our clinical observations as well as theoretical considerations now point to a whole body definition of occlusion— the Centralized Ideal (CI) occlusion-which is built on the three essential criteria.

The first criterion is a centralized jaw joint position, which can be easily determined by hip-level and ear palpation to feel the posterior aspect of the jaw joint. When there is no motion palpable in the ear canal upon opening and closing, the patient will be closing close to where their front teeth edges touch after opening wide and closing. This is synonymous to the situation where the jaw joint is aligned to function in its' anatomical best position on the fibrocartilage of the articular eminence. This is best accomplished by the trained dental professional team.

The second criterion is unrestricted free movement of all 29 cranial bones, which includes the tiny ossicles in the ear allowing for hearing to establish equal and opposing fluid, hydraulic motion of the cerebrospinal fluid within the dura enclosing the central nervous system without distortion or restriction to the structures suspended in them (brain, nerves, blood vessels etc.). In the head, normal cranial rhythm includes flexion and extension of the midline bones, and equal and opposing internal and external rotation of paired bones as they pivot at their sutures like the gears of an old-time watch. This most important awareness is from the medical field of Cranial Osteopathy. This is best accomplished by a professionally trained cranial osteopath.

The third criterion is balanced whole-body postural alignment. As described herein, it is desirable to achieve the balanced biomechanical model of tensegrity with the musculo-skeletal system with bones functioning as struts within the musculofascial system of tension/compression balanced in alignment and in motion. To achieve this requires releasing limitations and restrictions caused by previous injury and strain patterns, scars, and adhesions as well as their compensations. Inflammation, a common factor underlying most conditions, also creates adhesions interfering with the natural "slide & glide" motion of layers of unrestricted fascia. This is also affecting alignment in gravity with the proprioceptive system; eyes, ears, feet and multisensory integration and haptic perception and psychosocial adaptability. Balance contributes to centeredness, clarity, and an increased zone of adaptability/tolerance. Different posture, different jaw position and bite. This is best accomplished by those skilled in manual medicine, chiropractic, craniosacral and myofascial therapies, expanded concepts of physical therapy, bodyworkers, acupuncture and structural reintegration support.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A dental orthotic apparatus for aiding recovery from temporomandibular disorder (TMD), the dental orthotic apparatus comprising:
a first shell sized and configured for substantially fitting over an upper set of teeth of a patient, wherein the first shell has at least two cuspid protrusions sized and configured for substantially fitting over cuspid teeth of upper set of teeth, the at least two cuspid protrusions positioned at a terminating portion of the cuspid teeth, respectively;
a second shell sized and configured for substantially fitting over a lower set of teeth of the patient, the first and second shells configured for being removable from the upper and lower sets of teeth of the patient, respectively, wherein the first and second shells are configured for being frictionally held on the upper and lower sets of teeth of the patient, respectively; and
at least two cuspid indents formed in the second shell, wherein the at least two cuspid indents each have a sidewall and a middle interior portion, wherein when the first shell and second shell are positioned on the upper and lower sets of teeth of the patient, respectively, and when a jaw of the patient is closed, the at least two cuspid indents of the second shell substantially correspond to the two cuspid protrusions of the first shell, wherein a terminating end of the at least two cuspid protrusions is positioned fully below an entirety of an upper rim of the sidewall of the at least two cuspid indents, respectively, wherein movement of the upper cuspid protrusions is constrained in lateral, forward, and rear directions to align a jaw joint position of the patient by stabilizing mandibular condyles of the patient into a centralized relationship.

2. The apparatus of claim 1, wherein the first and second shells are substantially transparent.

3. The apparatus of claim 1, further comprising one or more buttons positioned on an exterior of the first or second shells.

4. The apparatus of claim 1, further comprising one or more elastic bands connected between one or more buttons on the first or second shells.

5. The apparatus of claim 1, wherein the at least two cuspid indents have lateral sidewalls configured for aligning with occlusal lateral sides of the teeth.

6. The apparatus of claim 5, wherein the at least two cuspid indents have a bowl shape.

7. The apparatus of claim 6, wherein the bowl shape is substantially shaped to receive upper cuspid protrusions.

8. The apparatus of claim 1, further comprising a filling portion of one or both of the first or second shells positioned for aligning with back teeth of the patient, wherein the filling portion fills in space between upper and lower back teeth of the patient.

9. The apparatus of claim 1, wherein terminating ends of the cuspid protrusions extend past an upper edge of the entirety of the perimeter of the sidewall of the cuspid indents when the jaw of the patient is closed.

10. The apparatus of claim 1, wherein the first and second shells comprise a plastic material.

11. A dental orthotic apparatus for aiding recovery from temporomandibular disorder (TMD), the dental orthotic apparatus comprising:
a first durable shell sized and configured for substantially fitting over an upper set of teeth of a patient, wherein the first durable shell has at least two cuspid protrusions sized and configured for substantially fitting over cuspid teeth of upper teeth, the at least two cuspid protrusions positioned at a terminating portion of the cuspid teeth, respectively;
a second durable shell sized and configured for substantially fitting over a lower set of teeth of the patient, the first and second durable shells configured for being removable from the upper and lower sets of teeth of the patient, respectively, wherein the first and second durable shells are configured for being frictionally held on the upper and lower sets of teeth of the patient, respectively;
at least two cuspid indents formed in the second durable shell, wherein the at least two cuspid indents each have a sidewall and a middle interior portion, wherein when the first durable shell and second durable shell are position on the upper and lower sets of teeth of the patient, respectively, and when a jaw of the patient is closed, the at least two cuspid indents of the second shell substantially correspond to the two cuspid protrusions of the first durable shell, wherein a terminating end of the at least two cuspid protrusions is positioned fully below an entirety of an upper rim of the sidewall of the at least two cuspid indents, respectively, wherein movement of the upper cuspid protrusions is constrained in lateral, forward, and rear directions such that when the first durable shell is worn on the upper teeth and the second durable shell is worn on the lower teeth, the at least two cuspid indents are adapted for receiving at least a portion of the at least two cuspid protrusions of the first durable shell when a jaw of the patient is closed to align a jaw joint position of the patient by stabilizing mandibular condyles of the patient into a centralized relationship; and a durable material inlayed or overlayed to at least one of the first and second durable shells in a location corresponding to a contact point between the first and second durable shells, wherein the durable material is a different material type than the first and second durable shells.

12. The apparatus of claim 11, wherein the durable material further comprises a ceramic material.

13. The apparatus of claim 11, wherein the durable material further comprises zirconia having a white color.

* * * * *